United States Patent

Nakagawa et al.

Patent Number: 5,373,002
Date of Patent: Dec. 13, 1994

[54] 2-(SUBSTITUTED PYRROLIDINYLTHIO) CARBAPENEM DERIVATIVES

[75] Inventors: Susumu Nakagawa; Norikazu Ohtake; Fumio Nakano; Koji Yamada; Ryosuke Ushijima; Satoshi Murase; Hiroshi Fukatsu, all of Okazaki, Japan

[73] Assignee: Banyu Pharmaceutical Co., Ltd., Tokyo, Japan

[21] Appl. No.: 950,717

[22] Filed: Sep. 25, 1992

Related U.S. Application Data

[63] Continuation-in-part of Ser. No. 674,971, Mar. 26, 1991, abandoned.

[30] Foreign Application Priority Data

Mar. 27, 1990 [JP] Japan ................. 2-77431
Apr. 12, 1990 [JP] Japan ................. 2-96654
Dec. 27, 1990 [JP] Japan ................. 2-414637

[51] Int. Cl.$^5$ ............. A01N 43/00; A61K 31/395; C07D 487/04
[52] U.S. Cl. ........................ 514/210; 540/350
[58] Field of Search ................. 540/350; 514/210

[56] References Cited

U.S. PATENT DOCUMENTS 4,921,852 5/1990 Murata et al. .
4,925,838 5/1990 Murata et al. .

Primary Examiner—Johann Richter
Assistant Examiner—Rebecca Cook
Attorney, Agent, or Firm—Oblon, Spivak, McClelland, Maier & Neustadt

[57] ABSTRACT

A compound of the formula:

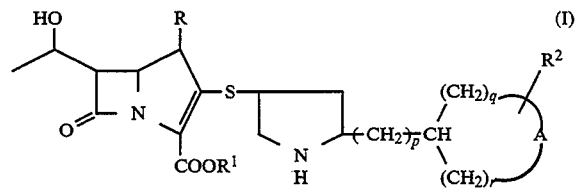

wherein R is a hydrogen atom or a methyl group, $R^1$ is a hydrogen atom or a negative charge, $R^2$ is a lower alkyl group, a lower alkyl group substituted with a hydroxyl group or —$COOR^3$ (wherein $R^3$ is a hydrogen atom or a lower alkyl group), A is =NH, =$NR^4$ or =$N(R^4)R^5$ (wherein each of $R^4$ and $R^5$ which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and q $+r \leq 6$; or a pharmaceutically acceptable salt or ester thereof.

13 Claims, No Drawings

2-(SUBSTITUTED PYRROLIDINYLTHIO) CARBAPENEM DERIVATIVES

This application is a continuation-in-part application of the application Ser. No. 07/674,971 having a filing date of Mar. 26, 1991, now abandoned.

BACKGROUND OF THE INVENTION

1. Field of the Invention

The present invention relates to novel carbapenem (7-oxo-1-azabicyclo[3.2.0]hept-2-en-2-carboxylic acid) compounds, and antibacterial agents containing such compounds as active ingredients, and a process for producing such compounds.

2. Discussion of Background

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of *Streptomyces cattleya* (J. Am. Chem. Soc., vol. 100, p.6491 (1978)), may be mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem, (5R,6S,8R)-3-[[2-(formimidoylamino)ethyl]thio]-6-(1-hydroxyethyl)-7-oxo-1-azabicyclo[3.2.0]hept-2-en-2-carboxylic acid monohydrate, obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against *Pseudomonas aeruginosa*, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DHP-I inhibitor like cilastatin (J. Antimicrob. Chemother., vol. 12 (Suppl. D), p. 1 (1983)). In recent years, imipenem has been frequently used for the treatment and prevention of infectious diseases. Consequently, highly methicillin resistant *Staphylococcus aureus* which is resistant to imipenem and imipenem resistant *Pseudomonas aeruginosa* are increasing in the clinical field. Imipenem does not show adequate treating effects against these resistant bacteria.

As the prior art closest to the present invention, U.S. Pat. No. 4,933,333 may be mentioned. This publication discloses carbapenem compounds having a 2-(aminocarbonyl or N-mono- or N,N-di-lower alkylaminocarbonyl)pyrrolidin-4-ylthio group at the 2-position of the carbapenem structure, represented by meropenem, SM-7338:

(4R,5S,6S,8R,2′S,4′S)-6-(1-hydroxyethyl)-4-methyl-3-[2-(N,N-dimethylaminocarbonyl)pyrrolidin-4-ylthio]-7-oxo-1-azabicyclo[3.2.0]hept-2-en-2-carboxylic acid, as a typical compound.

β-Lactam antibiotics exhibit selective toxicity against bacteria and show no substantial effects against animal cells. Therefore, they are widely used for treatment of infectious diseases caused by bacteria, as rare antibiotics having little side effects, and thus are highly useful drugs.

However, in recent years, highly methicillin resistant *Staphylococcus aureus* and resistant *Pseudomonas aeruginosa* have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria. Especially with respect to carbapenem compounds, it is desired to improve the antibacterial activities, to improve the stability against DHP-I, to reduce the toxicity against the kidney and to reduce side effects against the central nervous system.

The compounds disclosed in U.S. Pat. No. 4,933,333, particularly meropenem, have the stability against DHP-I substantially improved. However, the antibacterial activities against the above-mentioned highly methicillin resistant *Staphylococcus aureus* are not adequate, and a carbapenem compound having superior antibacterial activities, is desired.

The present inventors have made extensive researches with an aim to provide novel carbapenem compounds which have excellent antibacterial activities and which are resistant against DHP-I. As a result, they have found that carbapenem compounds of the present invention having, at the 2-position of the carbapenem structure, a group of the formula:

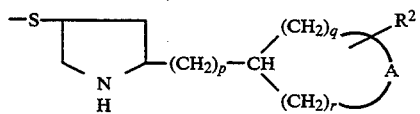

wherein $R^2$ is a lower alkyl group, a lower alkyl group substituted with a hydroxyl group or —COOR$^3$ (wherein $R^3$ is a hydrogen atom or a lower alkyl group), A is =NH, =NR$^4$ or =N(R$^4$)R$^5$ (wherein each of $R^4$ and $R^5$ which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and q+r≦6, are novel compounds not disclosed in any literatures, and that such compounds have strong antibacterial activities against gram positive bacteria such as *Staphylococcus aureus* and against gram negative bacteria including *Pseudomonas aeruginosa* and further exhibit excellent stability against DHP-I. The present invention has been accomplished on the basis of this discovery.

SUMMARY OF THE INVENTION

The present invention provides a compound of the formula:

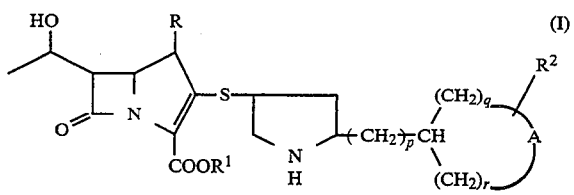

wherein R is a hydrogen atom or a methyl group, $R^1$ is a hydrogen atom or a negative charge, $R^2$ is a lower alkyl group, a lower alkyl group substituted with a hydroxyl group or —$COOR^3$ (wherein $R^3$ is a hydrogen atom or a lower alkyl group), A is =NH, =$NR^4$ or =$N(R^4)R^5$ (wherein each of $R^4 R^5 R^4$ and $R^5$ which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and $q+r \leq 6$; or a pharmaceutically acceptable salt or ester thereof.

The present invention also provides an antibacterial agent comprising an antibacterially effective amount of the compound of the formula (I) or a pharmaceutically acceptable salt or ester thereof, and a pharmaceutically acceptable carrier or diluent.

DETAILED DESCRIPTION OF THE PREFERRED EMBODIMENTS

Now, the present invention will be described in detail with reference to the preferred embodiments. Firstly, the symbols and terms used in this specification will be explained.

The compound of the present invention has a basic structure of the formula:

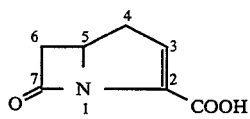

which is systematically referred to as a 7-oxo-1-azabicyclo[3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

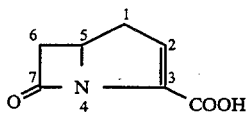

The present invention includes optical isomers based on the asymmetrical carbon atoms at the 1-position, 5-position, 6-position and 8-position of the carbapenem structure and stereoisomers. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

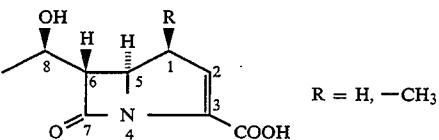

$R = H, —CH_3$

Also with respect to the 2-(alicyclic heteroring-substituted or alicyclic heteroring lower alkyl)pyrrolidin-4-ylthio group, the present invention includes isomers based on the asymmetrical carbon atoms at the 2-position and 4-position of the structure and in the side chain at the 2-position. Among these isomers, preferred are compounds of configuration and (2'R,4'R) configuration when p is 0, and compounds of (2'R,4'S) configuration and (2'S,4'R) configuration when p is an integer of from 1 to 3.

Further, with respect to the alicyclic heterocyclic group at the 2-position of the pyrrolidine there exist isomers based on asymmetrical carbons, and the present invention includes such isomers as well.

The lower alkyl group means a linear or branched alkyl group having from 1 to 6 carbon atoms, such as a methyl group, an ethyl group, a propyl group, an isopropyl group, a butyl group, a sec-butyl group, a tert-butyl group, a pentyl group or a hexyl group, preferably a methyl group, an ethyl group or a tert-butyl group.

The lower alkyl group substituted with a hydroxyl group means the above mentioned lower alkyl group substituted with a hydroxyl group, such as a hydroxymethyl group, a 1-hydroxyethyl group, a 2-hydroxyethyl group, a 1-hydroxypropyl group, a 2-hydroxypropyl group, a 3-hydroxypropyl group or a 4-hydroxybutyl group, preferably a hydroxymethyl group, a 2-hydroxyethyl group or 3-hydroxypropyl group, more preferably a hydroxymethyl group.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tert-butyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a tetrahydropyranyl group, a 2-propenyloxycarbonyl group, a p-nitrobenzyloxycarbonyl group and a tert-butyldimethylsilyl group.

The imino-protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)-methyl group or a trityl group; a lower alkanoyl group such as a formyl group, an acetyl group, a propionyl group, a butyryl group, an oxalyl group, a succinyl group or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2 -propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert-butoxycarbonyl group and a p-nitrobenzyloxycarbonyl group.

The alicyclic heterocyclic group on the pyrrolidin-4-ylthio group as the side chain at the 2-position of the carbapenem structure, is substituted at the 2-position of the pyrrolidine ring and has a structure of the formula:

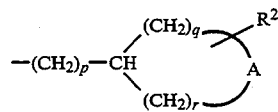

wherein $R^2$ is a lower alkyl group, a lower alkyl group substituted with a hydroxyl group or —$COOR^3$ (wherein $R^3$ is a hydrogen atom or a lower alkyl group), A is =NH, =$NR^4$ or =$N(R^4)R^5$ (wherein each of $R^4$ and $R^5$ which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and $q+r \leq 6$, $R^2$ may be substituted at any optional positions on carbon atoms constituting said alicyclic heteroring. $R^2$ is preferably a lower alkyl group, a lower alkyl group substituted with a hydroxyl group or —$COOR^3$ (wherein $R^3$ is as defined above), more preferably a linear lower alkyl group substituted with a terminal hydroxyl group such as a hydroxymethyl group, a 2-hydroxyethyl group or a 3-hydroxypropyl group. Particularly preferred among them is a hydroxymethyl group.

A represents a partial structure of said alicyclic heterocyclic group. As A, preferred is a case wherein A is =NH, =$NR^4$ or =$N(R^4)R^5$ (wherein each of $R^4$ and $R^5$ which may be the same or different, is a lower alkyl group or a lower alkyl group substituted with a hydroxyl group). Particularly preferred is a case wherein A is =NH, =$NR^4$ or =$N(R^4)R^5$ (wherein $R^4$ is a lower alkyl group substituted with a hydroxyl group and $R^5$ is a lower alkyl group or a lower alkyl group substituted with a hydroxyl group).

p is an integer of from 0 to 3, preferably 0 or 1, more preferably 1.

$R^1$ is a hydrogen atom or a negative charge. When the alicyclic heterocyclic group substituted at the 2-position of the pyrrolidine ring has a quaternary ammonium structure, $R^1$ represents a negative charge forming a pair with the ammonium ion, whereby the compound of the formula (I) forms an intramolecular salt.

The salt of the compound of the formula (I) is a common pharmaceutically acceptable salt and may, for example, be a salt at the carboxyl group at the 3-position of the carbapenem structure, or at the pyrrolidine base or the base of the alicyclic heterocyclic group in the side chain at the 2-position of the carbapenem structure.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base or at the base of the alicyclic heterocyclic group includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo-1,3-dioxol-4-yl)methyl group such as a (5-methyl-2-oxo-1,3-dioxol-4-yl)methyl group.

Among the compound of the formula (I), preferred is, for example, (1R, 5S, 6S)-2-[(2R, 4S)-2-[(2S, 4R)-2-carboxypyrrolidin-4-ylmethyl]pyrrolidin-4-ylthio]-6-[(R)-1-hydroxyethyl]-1-methyl-1-carbapen-2-em-3-carboxylic acid, (1R, 5S, 6S)-6-[(R)-1-hydroxyethyl]-2-[(2R, 4S)-2-[(2S, 4R)-2-hydroxymethylpyrrolidin-4-ylmethyl]pyrrolidin-4-ylthio]-1-methyl-1-carbapen-2-em-3-carboxylic acid (1R, 5S, 6S)-6-[(R)-1-hydroxyethyl]-1-methyl-2-[(2R, 4S)-2-[(2R, 4S)-2-methylpyrrolidin-4-ylmethyl]pyrrolidin-4-ylthio]-1-carbapen-2-em-3-carboxylic acid, (1R, 5S, 6S)-6-[(R)-1-hydroxyethyl]-2-[(2S, 4S)-2-[N-(2-hydroxyethyl)piperidin-4-yl]pyrrolidin-4-ylthio]-1-methyl-1-carbapen-2-em-3-carboxylic acid, (1R, 5S, 6S)-6-[(R)-1-hydroxyethyl]-2-[(2S, 4S)-2-(3-hydroxymethylpyrrolidin-4-yl)pyrrolidin-4-ylthio]-1-methyl-1-carbapen-2-em-3-carboxylic acid or (1R, 5S, 6S)-6-[(R)-1-hydroxyethyl]-2-[(2S, 4S)-2-[N-(2-hydroxyethyl)pyrrolidin-3-yl]pyrrolidin-4-ylthio]-1-methyl-1-carbapen-2-em-3-carboxylic acid. More preferred is (1R, 5S, 6S)-6-[(R)-1-hydroxyethyl]-2-[(2R, 4S)-2-[(2S, 4R)-2-hydroxymethylpyrrolidin-4-ylmethyl]pyrrolidin-4-ylthio]-1-methyl-1-carbapen-2-em-3-carboxylic acid.

Now, the process for producing the compound of the present invention will be described.

An activating reagent is reacted to a compound of the formula:

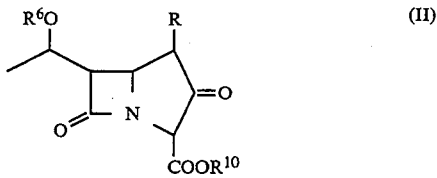

wherein R is a hydrogen atom or a methyl group, R⁶ is a hydrogen atom or a hydroxyl-protecting group, and R¹⁰ is a hydrogen atom or a carboxyl-protecting group, in an inert organic solvent in the presence of a base to form a reactive derivative of the formula (II'):

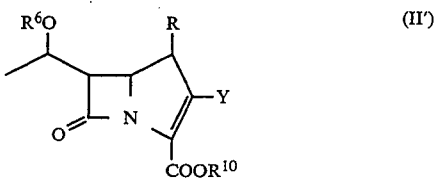

wherein R, R⁶ and R¹⁰ are as defined above, and Y is a leaving group.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols, of the base and from 1 to 1.2 mols of the activating reagent are used per mol of the compound of the formula (II).

The reaction is conducted usually within a temperature range of from −40° to 50° C., preferably from −20° to 20° C., and usually completed quantitatively in from 0.5 to 3 hours.

After completion of the reaction, the reaction product is treated in accordance with a usual method to obtain the reactive derivative (II') of the compound of the formula (II) quantitatively.

The reaction of the reactive derivative of the formula (II') with a compound of the formula:

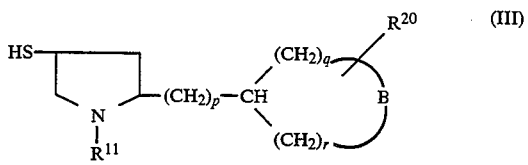

wherein R¹¹ is a hydrogen atom or an imino-protecting group, R²⁰ is a lower alkyl group, a lower alkyl group substituted with a hydroxyl group which may be protected or —COOR³⁰ (wherein R³⁰ is a hydrogen atom, a lower alkyl group or a carboxyl-protecting group), B is =NH, =NR⁴⁰ or =N(R⁴⁰)R⁵⁰ (wherein each of R⁴⁰ and R⁵⁰ which may be the same or different is an imino-protecting group, a lower alkyl group or a lower alkyl group substituted with a hydroxyl group which may be protected), and p, q and r are as defined above, is conducted using the above mentioned inert organic solvent and base to form a compound of the formula:

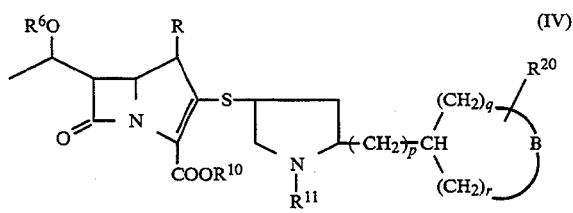

wherein R, $R^6$, $R^{10}$, $R^{11}$, $R^{20}$, B, p, q and r are as defined above.

The reaction is conducted using from 1 to 2 mols, preferably from 1 to 1.5 mols, of the base and from 1 to 1.2 mols of the compound of the formula (III), per mol of the reactive derivative of the formula (II'). The reaction is conducted usually within a temperature range of from −40° to 50° C., preferably from −20° to 20° C., and the reaction is completed usually in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mols, preferably from 2.5 to 3.5 mols, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, a compound of the formula (I) can be obtained, if necessary, by conducting a reaction for removing a protecting group for a hydroxyl group, an imino group and a carboxyl group.

For the removal of the protecting groups, the method varies depending upon the type of the protecting groups. However, the removal can be conducted in accordance with conventional methods, for example, by solvolysis, by chemical reduction or by hydrogenation.

For example, when in the above formula (IV), the protecting group for the hydroxyl group and/or for the imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the imino group is an allyloxycarbonyl group, and the protecting group for the carboxyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587–590 (1982) and method by F. Guibé, the same literature, vol. 52, p. 4,984–4,993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium compound complex useful for this reaction includes, for example, palladium-carbon, palladium hydroxide-carbon, palladium(II) chloride, palladium(II) acetate, tetrakis(triphenylphosphine)palladium (O), tetrakis(triphenoxyphosphine)palladium (O), tetrakis(triethoxyphosphine)palladium (O), bis[ethylenebis(diphenylphosphine)]palladium (O), tetrakis[tri(2-furyl)phosphine]palladium (O), bis(triphenylphosphine)palladium(II) chloride and bis(triphenylphosphine)palladium(II) acetate.

The allyl group-capturing agent may, for example, be dimedone, formic acid, acetic acid, ammonium formate, sodium formate, sodium 2-ethylhexanoate, potassium 2-ethylhexanoate, pyrrolidine, piperidine and tributyltin hydride.

The reaction is conducted usually within a temperature range of from −10° to 50° C., preferably from 0° to 30° C. using from 0.01 to 0.5 mol of the catalyst and from 1 to 6 mols of the nucleophilic agent relative to 1 mol of the compound of the formula (IV), and the reaction is completed usually in from 0.5 to 3 hours.

Further, when in the above formula (IV), the protecting group for the hydroxyl group and/or the imino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, p. 192–196 (1974)).

After completion of the reactions for removing the protecting groups, the compound of the formula (I) can be isolated by usual treatment such as column chromatography using silica gel or adsorptive resin, freeze-drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group or a phthalidyl group, such an ester will be physiologically hydrolyzed in vivo. Therefore, such a compound can directly be administered to a human being or to an animal without preliminarily removing the protecting group.

The compound of the formula (I) can be converted to a pharmaceutically acceptable salt or ester by a conventional method.

The starting material of the formula (II) can be prepared, for example, by a method by Salzmann et al. when R is a hydrogen atom (J. Am. Chem. Soc., vol. 102, p.6161–6163 (1981)) or by a method by Shih et al. when R is a methyl group (Heterocycles, vol. 21, p.29–40 (1984)).

The starting material of the formula (III) can be synthesized by the following method.

The hydroxyl group (—OR$^{12}$) of the compound 1 is activated by a usual method, and a thioacetate such as potassium thioacetate is reacted thereto to convert it to an acetylthio derivative 3, followed by alkali or acid hydrolysis to obtain a thiol derivative of the formula (III).

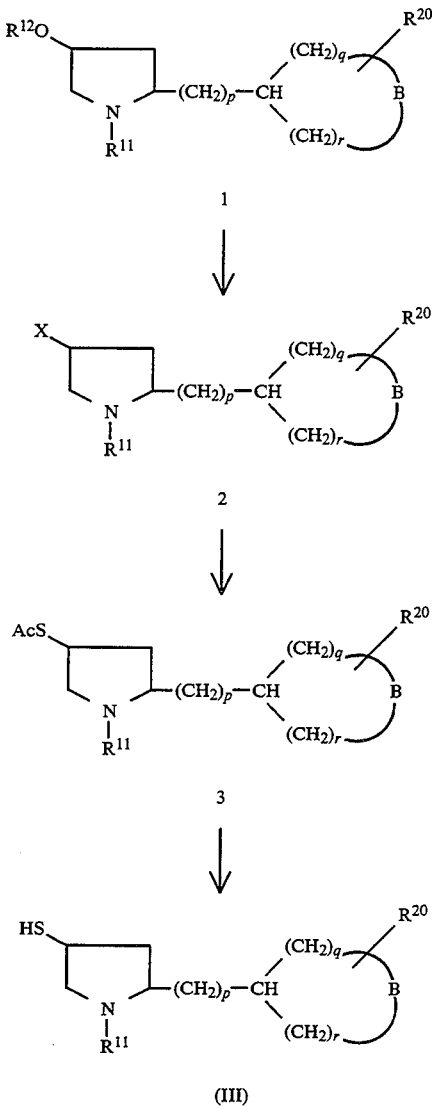

In the above formulas, R$^{12}$ is a hydrogen atom or a hydroxyl-protecting group, X is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group, Ac is an acetyl group, and R$^{11}$, R$^{20}$, B, p, q and r are as defined above A group of compounds having the formula 1 can be prepared in accordance with the methods described in the Reference Examples.

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76–79 (1981)). One platinum loopful of each test microorganism incubated overnight in Mueller Hinton broth, was inoculated to Mueller Hinton agar (inoculum size: 10$^6$ CFU/ml). Such culture media contained antibacterial agents in various concentrations. After incubation at 37° C. for 16 hours, the minimum inhibitory concentrations (MIC: μg/ml) were measured.

The results of the antibacterial activities of the compounds of the present invention are shown in Table 1.

The DHP-I susceptibility was quantitatively analyzed by the method by Kropp et al., Antimicrob. Agents Chemother., vol. 22, p. 62–70 (1982), whereby the smaller the numerical value representing the ratio to imipenem (=1.0), the higher the stability. The DHP-I susceptibility of the compounds of the present invention were compared with imipenem and meropenem. The results are shown also in Table 1.

TABLE 1

| Minimum Inhibitory Concentration (MIC: μg/ml) and DHP-I susceptibility | | | |
|---|---|---|---|
| | Example 2 | Meropenem | Imipenem |
| P. aeruginosa MB5000 | 0.1 | 0.39 | 1.56 |
| P. aeruginosa MB5002 | 0.39 | 6.25 | 3.13 |
| P. aeruginosa AKR17 | 1.56 | 3.13 | 6.25 |
| DHP-I susceptibility | <0.05 | 0.12 | 1.0 |

*β-lactamase producing microorganism

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The compounds of the present invention exhibit excellent antibacterial activities particularly against Methicillin resistant Staphylococcus aureus and against thienamycin resistant Pseudomonas aeruginosa. Further, in tests by using mice, etc. for prevention of infection caused by various bacteria, the compounds of the present invention show treating effects superior to meropenem against particularly Staphylococcus aureus and Pseudomonas aeruqinosa while reflecting excellent antibacterial activities in vitro.

The compounds of the present invention show change of the concentration in blood and biological half-life superior to imipenem and meropenem with respect to Rodentia such as mouse and Primates such as rhesus monkey.

The compounds of the present invention are very stable against DHP-I although the stability varies depending upon the individual compounds, and they are excellent also in the physicochemical stability and in the solubility in water.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age,-the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2-carboxyethylthio)-2-(2,2-dimethylcyclopropanecarboxamide)-2-heptenoate] (Japanese Unexamined Patent Publication No. 81518/1981; European Pat. No. 28,778; J. Med. Chem., vol. 30, p. 1074 (1987)).

Now, the present invention will be described in further detail with reference to Examples and Reference Examples. However, it should be understood that the present invention is by no means restricted by such specific Examples.

In the thin layer chromatography in the Examples and Reference Examples, silica gel 60F245 (Merck) was used as the plate, and an ultraviolet detector was used as a detecting device. As the silica gel for the column, Wakogel TM C-300 (Wako Junyaku) was used, and as the silica gel for reversed phase column, LC-SORB TM SP-B-ODS (Chemco) or YMC-GEL TM ODS-AQ 120-S50 (Yamamura Chemical Laboratories) was used. As the high pressure liquid chromatograph, JASCO 800 series (Nippon Bunko) was used. When the NMR spectrum was measured using a dimethyl sulfoxide-$d_6$ or chloroform-d solution, tetramethylsilane (TMS) was used as the internal standard, and when measured using a deuterium oxide solution, 2,2-dimethyl-2-silapentane-5-sulfonate (DSS) was used as the internal standard, and the measurement was conducted by means of XL-200 (200 MHz; Varian) model spectrometer. All δ values are shown by ppm.

The meanings of the abbreviations used for the NMR measurement are as follows:
s: singlet
d: doublet
t: triplet
q: quartet
ABq: AB-type quartet
dd: double doublet
m: multiplier
br: broad
J: coupling constant
Hz: hertz
CDCl$_3$: chloroform-d
CD$_3$OD: methanol-$d_4$
D$_2$O: deuterium oxide The meanings of the abbreviations used in the reaction formulas are as follows:
Ac: acetyl group
Boc: tert-butoxycarbonyl group
Bzl: benzyl group
Et: ethyl group
Me: methyl group
Ms: methanesulfonyl group
Ph: phenyl group
PNB: p-nitrobenzyl group
PNZ: p-nitrobenzyloxycarbonyl group
TBDMS: tert-butyldimethylsilyl group
THP: tetrahydropyranyl group

EXAMPLE 1

(1R, 5S, 6S)-2-[(2R, 4S)-2-[(2S, 4R)-2-carboxypyrrolidin-4-ylmethyl ]pyrrolidin-4-yl thio ]-6-[(R)-1-hydroxyethyl]-1-methyl-1-carbapen-2-em-3-carboxylic acid

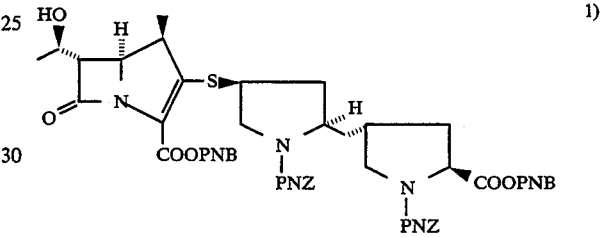

1)

A 2N sodium hydroxide solution ( 0.5 ml, 1.00 mmol ) was added to a solution of (2R, 4S)-4-acetylthio-N-(p-nitrobenzyloxycarbonyl)-2-[(2S, 4R)-N-(p-nitrobenzyloxycarbonyl)-2-(p-nitrobenzyloxycarbonyl)pyrrolidin-4-ylmethyl]pyrrolidine (790 mg, 1.03 mmol) in methanol (16 ml) at 0° C. under a nitrogen stream, and the solution was stirred at the same temperature for 30 minutes. After neutralizing the reaction solution with a 6N hydrochloric acid (0.17 ml, 1.02 mmol), ethyl acetate was added thereto. The mixture was washed with a saturated sodium chloride aqueous solution, then dried over anhydrous magnesium sulfate and concentrated.

To a solution of p-nitrobenzyl (1R, 5S, 6S)-2-diphenoxyphosphoryloxy-6-[(R)-1-hydroxyethyl]-1-methyl-1-carbapen-2-em-3-carboxylate (612 mg, 1.03 mmol) in acetonitrile (30 ml), a solution of the thiol obtained by the above reaction in acetonitrile (11 ml) and then N,N-diisopropylethylamine (0.19 ml, 1.07 mmol) were dropwise added under cooling with ice in a nitrogen stream. The reaction mixture solution was stirred at 0° C. for 7 hours, and ethyl acetate (130 ml) was added thereto. The organic layer was washed with water and a saturated sodium chloride aqueous solution, then dried over anhydrous magnesium sulfate and concentrated under reduced pressure. The residue was subjected to silica gel column chromatography (Wakogel TM C-300, ethyl acetate) to obtain p-nitrobenzyl (1R, 5S, 6S)-2-[(2R, 4S)-N-(p-nitrobenzyloxycarbonyl)-2-[(2S, 4R)-N-(p-nitrobenzyloxycarbonyl)-2-(p-nitrobenzyloxycarbonyl)pyrrolidin-4-ylmethyl]pyrrolidin-4-ylthio]-1-carbapen-2-em-3-carboxylate (886 mg, yield: 72%).

NMR(CDCl$_3$)δ: 1.25(3H,m); 1.37(3H,d,J=6.27Hz), 1.57-2.65 (7H,m) , 3.03-4.58 ( 11H,m), 5.10-5.29 ( 7H,m), 5.50(1H,d,J=13.86Hz), 7.36-7.52(6H,m), 7.64(2H,d,J=8.91Hz), 8.12-8.24(8H,m)

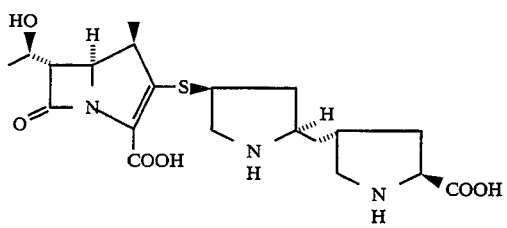
2)

A mixture of the compound obtained in the above reaction (950 mg, 0.79 mmol), tetrahydrofuran (30 ml), ethanol (5 ml), 0.1M sodium 3-morpholinopropanesulfonate buffer solution (pH7.0, 30 ml) and 10% palladium-carbon catalyst (470 mg) was shaken under a hydrogen pressure of 3 atm at room temperature for 3 hours. The catalyst was filtered off from the reaction mixture, and the filtrate was washed with ethyl acetate (35 ml), and insoluble matters in the aqueous layer were filtered off. The filtrate thus obtained was concentrated to a volume of about 26 ml. The residue was subjected to reversed phase column chromatography (YMC™ ODS-AQ 120-S50, 10% methanol aqueous solution). The desired fraction was concentrated and freeze-dried to obtain the above identified compound (106 mg, yield: 31%).

NMR(D$_2$O)δ: 1.23(3H:,d,J=7.26Hz), 1.30(3H,d,J=6.27Hz), 1.64-1.75(1H,m), 1.99-2.12(3H,m), 2.31-2.41(2H,m), 2.75-2.85(1H,m), 2.99-3.07(1H,dd,J=9.57,11.55Hz), 3.34-3.42(2H,m), 3.47-3.50(1H,dd,J=2.31,5.93Hz), 3.64-3.79(4H,m), 3.98-4.07(1H,m), 4.22-4.31(3H,m)

HPLC:
Column: YMC™-Pack AQ-302 S-5 120A ODS, 4.6φ×150 mm,
Eluent: 20% methanol-phosphate buffer solution (pH6.5)
Flow rate: 1.0 ml/min
Temperature: 40° C.
UV: 290 nm
Retention time: 2.14 min

EXAMPLE 2

(1R, 5S, 6S)-6-[(R)-1-hydroxyethyl]-2-[(2R, 4S)-2-[(2S, 4R)-2-hydroxymethylpyrrolidin-4-ylmethyl]pyrrolidin-4-ylthio]-1-methyl-1-carbapen-2-em-3-carboxylic acid

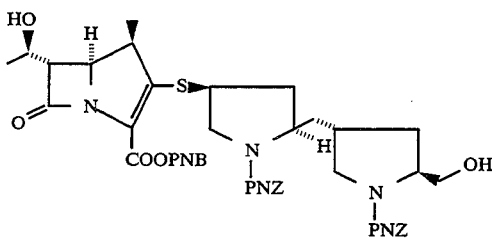
1)

(2R, 4S)-4-acetylthio-2-[(2S,4R)-2-hydroxymethyl-N-(p-nitrobenzyloxycarbonyl)pyrrolidin-4-ylmethyl]-N-(p-nitrobenzyloxycarbonyl)pyrrolidine (150 mg, 0.24 mmol) was dissolved in a solution comprising methylene chloride (0.5 ml) and methanol (1.5 ml). A 2N sodium hydroxide aqueous solution (0.18 ml, 0.36 mmol) was dropwise added under cooling with ice in a nitrogen stream, and the reaction mixture solution was stirred for 20 minutes. After a 6N hydrochloric acid (0.06 ml, 0.36 mmol) was added to the reaction solution, the solution was poured into a saturated sodium chloride aqueous solution, then extracted with methylene chloride, and dried over anhydrous magnesium sulfate and concentrated under reduced pressure. By using the compound thus obtained and p-nitrobenzyl (1R, 5S, 6S)-2-diphenoxyphosphoryloxy-6-[(R)-1-hydroxyethyl]-1-methyl-1-carbapen-2-em-3-carboxylate (130 mg, 0.22 mmol), the same procedure as in Example 1-1) was carried out to obtain p-nitrobenzyl (1R, 5S, 6S)-6-[(R)-1-hydroxyethyl]-2-[(2R, 4S)-2-[(2S, 4R)-2-hydroxymethyl-N-(p-nitrobenzyloxycarbonyl)pyrrolidin-4-ylmethyl]pyrrolidin-4-ylthio]-1-methyl-1-carbapen-2-em-3-carboxylate (129 mg, yield: 58%).

NMR (CDCl$_3$)δ: 1.27(3H,d,J=6Hz), 1.37(3H,d,J=6Hz), 1.50-2.40(6H,m), 2.62(1H,m), 3.08(1H,m), 3.30(4H,m), 3.62(4H,m), 3.92(2H,m), 4.27(2H,m), 5.22(5H,m), 5.50(1H,d,J=12Hz), 7.50(4H,m), 7.64(2H,d,J=SHz), 8.22(6H,d,J=8Hz)

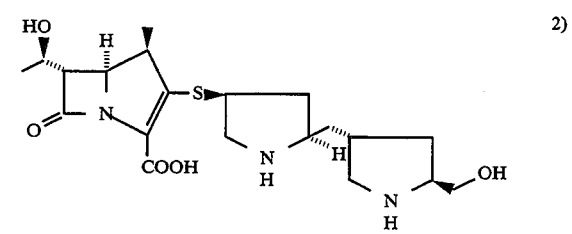
2)

A mixture of the compound obtained by the above reaction (7.1 g, 7.73 mmol), tetrahydrofuran (213 ml), ethanol (35.5 ml), 0.2M sodium 3-morpholinopropanesulfonate buffer solution (pH7.0, 213 ml) and 10% palladium-carbon catalyst (2.4 g) was shaken under a hydrogen pressure of 45 psi (about 3 atm) at 10° C. for 6 hours. The reaction mixture obtained was treated and purified in the same manner as in Example 1-2) to obtain the above-identified compound (574 mg, yield: 17.4%).

NMR(D$_2$O)δ: 1.21(3H,d,J=6Hz), 1.28(3H,d,J=6Hz), 1.70(1H,m), 1.78-2.20(4H,m), 2.48(1H,m), 2.82(1H,m), 3.03(1H,m), 3.36(1H,m), 3.46(1H,dd,J=3,6Hz), 3.56-4.06(8H,m), 4.24(2H,m)

HPLC:
Eluent: 20% methanol/phosphate buffer solution
Flow rate: 0.8 ml/min
UV: 300 nm
Retention time: 3.34 min
(Conditions other than the above are the same as in Example 1.)

EXAMPLE 3

(1R, 5S, 6S)-6-[(R)-1-hydroxyethyl]-1-methyl-2-[(2R, 4S)-2-[(2R, 4S)-2-methylpyrrolidin-4-ylmethyl]pyrrolidin-4-ylthio]-1-carbapen-2-em-3-carboxylic acid

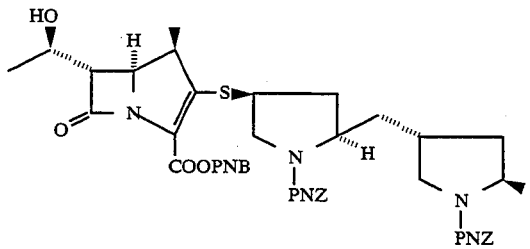
1)

The same procedure as in Example 2-1) was carried out by using (2R, 4S)-4-acetylthio-2-[(2R,4S)-2-methyl-N-(p-nitrobenzyloxycarbonyl)pyrrolidin-4-ylmethyl]-N-(p-nitrobenzyloxycarbonyl)pyrrolidine (420 mg, 0.71 mmol) and p-nitrobenzyl (1R, 5S, 6S)-2-diphenoxyphosphoryloxy-6-[(R)-1-hydroxymethyl]-1-methyl-1-carbapen-2-em-3 -carboxylate (378 mg, 0.64 mmol) to obtain p-nitrobenzyl (1R, 5S, 6S)-6-[(R)-1-hydroxyethyl]-1-methyl-2-[(2R, 4S)-2-[(2R, 4S)-2-methyl-N-(p-nitrobenzyloxycarbonyl)pyrrolidin-4-ylmethyl]pyrrolidin-4-ylthio]-1-carbapen-2-em-3-carboxylate (440 mg, yield: 69%).

NMR (CDCl$_3$)δ: 1.20(3H,m), 1.27(3H,$^{d,J}$=6Hz), 1.37(3H,d,J=6Hz), 1.50–1.90(4H,m), 2.00–2.40(2H,m), 2.62(1H,m), 2.98(1H,m), 3.26(2H,m), 3.98(4H,m), 4.26(2H,m), 5.20(5H,m), 5.50(1H,d,$^J$=14Hz), 7.50(4H,d,J=9Hz), 7.64(2H,d,J=9Hz), 8.21(6H,d,J=9Hz)

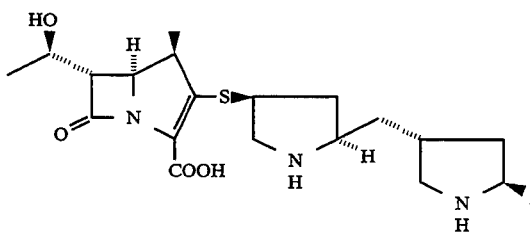
2)

The compound obtained in the above reaction ( 440 mg, 0.49 mmol) was treated and purified in the same manner as in Example 1-2) to obtain the above-identified compound (25 mg, yield: 12.4%).

NMR(D$_2$O)δ: 1.22(3H,d,J=7Hz), 1.29(3H,d,J=7Hz), 1.37(3H,d,J=7Hz), 1.72(1H,m), 2.02(4H,m), 2.55(1H,m), 2.80(1H,m), 2.97(1H,dd,J=8,12Hz), 3.41(2H,m), 3.47(1H,dd,J=2,6Hz), 3.54–3.80(3H,m), 3.90(1H,q,J=7Hz), 4.03(2H,m)

HPLC:

Eluent: 20% methanol/pH6.5 phosphate buffer solution
Flow rate: 0.8 ml/min
UV: 300 nm
Retention time: 4.08 min (Conditions other than the above are the same as in Example 1.)

EXAMPLE 4

(1R, 5S, 6S)-6-[(R)-1-hydroxyethyl]-2-[(2S, 4S)-2-[N-(2-hydroxyethyl)piperidin-4-yl]pyrrolidin-4-ylthio]-1-methyl-1-carbapen-2-em-3-carboxylic acid hydrochloride

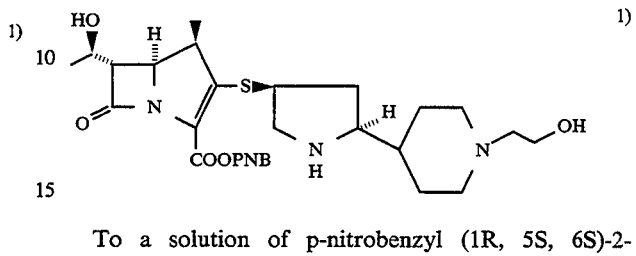
1)

To a solution of p-nitrobenzyl (1R, 5S, 6S)-2-diphenoxyphosphoryloxy-6-[(R)-1-hydroxyethyl]-1-methyl-1-carbapen-2-em-3-carboxylate (8.92 g, 15 mmol) in acetonitrile (600 ml), N,N-diisopropylethylamine (10.7 ml, 61.5 mmol) was added under cooling with ice and (2S, 4S)-2-[N-(2-hydroxyethyl)piperidin-4-yl]-4-mercaptopyrrolidine dihydrochloride (4.80 g, 15.8 mmol) was further added in limited amount. After the mixture was stirred at the same temperature for 19 hours, the reaction solution was concentrated to a volume of 300 ml and stirred under cooling with ice for 2 hours. Precipitates were collected by filtration and washed with acetonitrile, followed by drying to obtain p-nitrobenzyl (1R, 5S, 6S)-6-[(R)-1-hydroxyethyl]-2-[(2S, 4S)-2-[N-(2-hydroxyethyl)piperidin-4-yl]pyrrolidin-4-ylthio]-1-methyl-1-carbapen-2-em-3-carboxylate (4.77g, yield: 55.4%).

IR (KBr)cm$^{-1}$: 1760, 1510, 1340

NMR (CDCl$_3$+CD$_3$OD)δ: 1.28(3H,d,J=7Hz), 1.34(3H,d,J=6Hz), 1.65(1H,m), 1.9(1H,m), 1.95–2.12(2H,m), 2.12–2.5(5H,m), 2.5–2.6(2H,m), 2.77(1H,m), 2.9–3.05(2H,m), 3.1–3.45(3H,m), 3.55–3.72(3H,m), 4.13–4.3(2H,m), 5.25(1H,d,J=14Hz), 5.49(1H,d,J=14Hz), 7.65(1H,d,J=9Hz), 8.22(1H,d,J=9Hz)

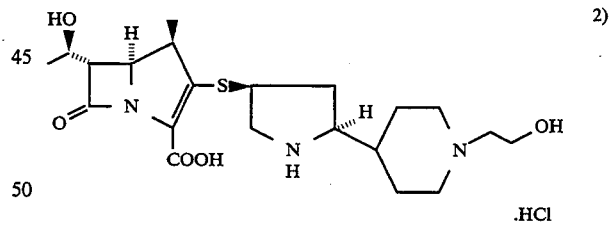
2)

.HCl

To a solution of the compound obtained by the above reaction (4.77 g, 8.3 mmol) in methanol (60 ml), a 0.25M sodium 3-morpholinopropanesulfonate buffer solution (120 ml), tetrahydrofuran (60 ml) and 10% palladium-carbon catalyst (3.3 g) were added and stirred in a hydrogen stream at room temperature for 3 hours. The catalyst was filtered off from the reaction mixture, and the organic solvent was distilled off under reduced pressure, and insoluble matters in the aqueous layer were filtered off. Then, filtrate obtained was concentrated to a volume of about 100 ml and the concentrate was subjected to reversed phase column chromatography (YMC·GEL ™ ODS-AQ 120-S50, 100 ml, 15% methanol aqueous solution). The desired fraction was concentrated and freeze-dried to obtain the above-identified compound (2.81 g, yield: 71.1%).

IR (KBr)cm$^{-1}$: 1755, 1595, 1395

NMR(D$_2$O)δ: 1.21(3H,d,J=7Hz), 1.28(3H,d,J=6Hz), 1.58–1.85(3H,m), 2.0–2.2(3H,m), 2.78(1H,m), 3.0–3.2(2H,m), 3.25–3.77(9H,m), 3.87–3.97(2H,m), 4.27(1H,m), 4.17–4.3(2H,m)

EXAMPLE 5

(1R, 5S, 6S)-6-[(R)-hydroxyethyl]-2-[(2S, 4S)-2-(3-hydroxymethylpyrrolidin-4-yl)pyrrolidin-4-ylthio]-1-methyl-1-carbapen-2-em-3-carboxylic acid diastereomer A

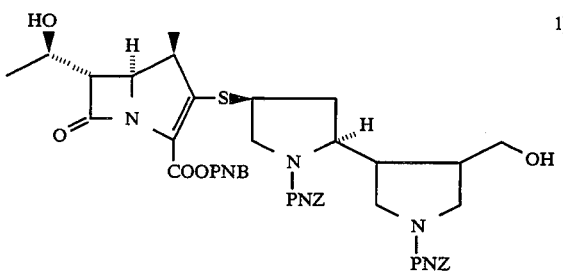

The same procedure as in Example 1-1) was carried out by using (2S, 4S)-2-[3-hydroxymethyl-N-(p-nitrobenzyloxycarbonyl)pyrrolidin-4-yl]-4-mercapto-N-(p-nitrobenzyloxycarbonyl)pyrrolidine diastereomer A (3.34 g, 5.42 mmol, compound of Reference Example 5) and p-nitrobenzyl (1R, 5S, 6S)-2-diphenoxyphosphoryloxy-6-[(R)-1-hydroxyethyl]-1-methyl-1-carbapen-2-em-3-carboxylate (3.22 g, 5.42 mmol) to obtain p-nitrobenzyl (1R, 5S, 6S)- 6-[(R)-1-hydroxyethyl]-2-[(2S,4S)-2-[3-hydroxymethyl-N-(p-nitrobenzyloxycarbonyl)pyrrolidin-4-yl]-N-(p-nitrobenzyloxycarbonyl)-pyrrolidin-4-ylthio]-1-methyl-1-carbapen-2-em-3-carboxylate diastereomer A (2.81 g, yield: 57.3%).

IR (KBr)cm$^{-1}$: 1740, 1700, 1520

NMR (CDCl$_3$)δ: 1.27(3H,d,J=7Hz), 1.36(3H,d,J=6Hz), 1.74(2H,m), 2.17(3H,m), 2.53(1H,m), 2.96(1H,m), 3.2–3.4(4H,m), 3.45–3.70(4H,m), 4.1–4.3(3H,m), 5.2–5.6(6H,m)

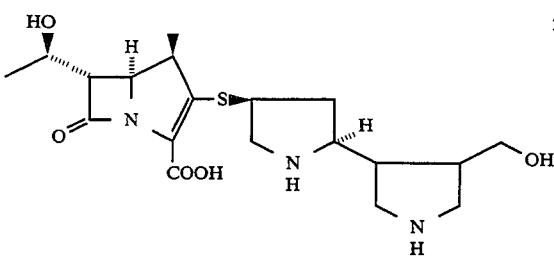

The same procedure as in Example 1-2) was carried out by using the compound obtained by the above reaction (2.81 9, 3.11 mmol) to obtain the above-identified compound (776 mg, yield: 55.8%).

IR (KBr)cm$^{-1}$: 3400, 1760, 1590

NMR (D$_2$O)δ: 1.22(3H,d,J=7Hz), 1.29(3H,d,J=6Hz), 1.81(1H,m), 2.55(1H,m), 2.64–2.84(2H,m), 3.2–3.27(2H,m), 3.30–3.48(3H,m), 3.55–3.67(2H,m), 3.70–3.81(4H,m), 4.03(1H,m), 4.20–4.29(2H,m)

UV λ$_{max}$ (0,1N 3-morpholinopropanesulfonic acid buffer solution, pH7): 299.5 nm (ε:8640)

EXAMPLE 6

(1R, 5S, 6S)-6-[(R)-1-hydroxyethyl ]-2-[(2S, 4S)-2-(3-hydroxymethylpyrrolidin-4-yl)pyrrolidin-4-ylthio]-1-methyl-1-carbapen-2-em-3-carboxylic acid diastereomer B

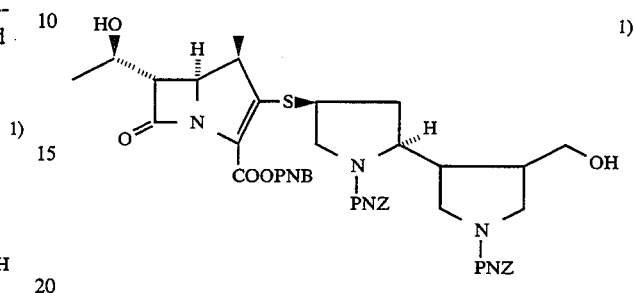

The same procedure as in Example 1-1) was carried out by using (2S, 4S)-2-[3-hydroxymethyl-N-(p-nitrobensyloxycarbonyl)pyrrolidin-4-yl]-4-mercapto-N-(p-nitrobenzyloxycarbonyl)pyrrolidine diastereomer B (6.21 g, 11.1 mmol, compound of Reference Example 6) to obtain p-nitrobenzyl (1R, 5S, 6S)-6-[(R)-1-hydroxyethyl]-2-[(2S, 4S)-2-[3-hydroxymethyl-N-(p-nitrobenzyloxycarbonyl)pyrrolidin-4-ylthio]-1-methyl-1-carbapen-2-em-3-carboxylate diastereomer B (8.06 g, yield: 88.4%).

IR (KBr)cm$^{-1}$: 1140, 1700, 1520

NMR (CDCl$_3$)δ: 1.27(3H,d,J=7Hz), 1.37(3H,d,J=6Hz), 1.62(2H,m), 2.35–2.80(4H,m), 3.10–3.4(4H,m), 3.5–5.50(2H,d,J=14Hz), 7.51(4H,d,J=9Hz), 7.65(2H,d,J=9Hz), 8.22(6H,d,J=9Hz)

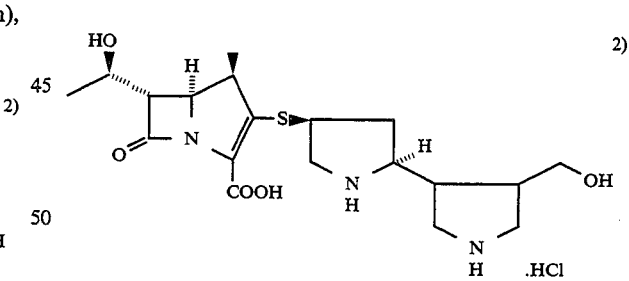

The same procedure as in Example 1-2) was carried out by using the compound obtained by the above reaction (8.06 g, 8.91 mmol) to obtain the above-identified compound (2.06 g, yield: 51.7%).

IR (KBr)cm$^{-1}$: 3400, 1760, 1590

NMR (D$_2$O)δ: 1.16(3H,d,J=7Hz), 1.22(3H,d,J=6Hz), 1.77 (1H,m), 2.48(1H,m), 2.59–2.84(2H,m), 3.17–3.42(5H,m), 3.50(1H,m), 3.6–3.69(4H,m), 3.78(1H,m), 3.98(1H,m), 4.14–4.23(2H,m)

UV λ$_{max}$ (0.1M 3-morpholinopropanesulfonic acid buffer solution, pH7): 299.5 nm (ε: 9140)

EXAMPLE 7

(1R, 5S, 6S)-6-[(R) -1-hydroxyethyl],2-[(2S, 4S)-2-[N-(2-hydroxyethyl ) pyrrolidin-3-yl]pyrrolidin-4-ylthio]-1-methyl-1-carbapen-2-em-3-carboxylic acid diastereomer A

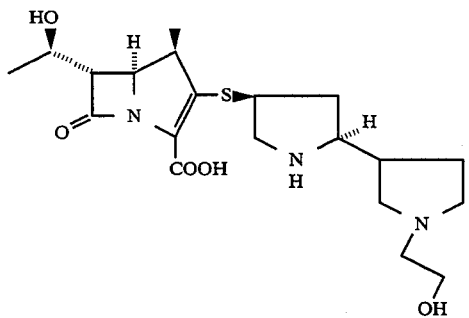

The same procedure as in Example 1-1) was carried out by using (2S, 4S)-2-[N-(2-hydroxyethyl)pyrrolidin-3-yl]-4-mercaptopyrrolidine diastereomer A dihydrochloride (3.5 g, 11.9 mmol, compound of Reference Example 7) to obtain p-nitrobenzyl (1R, 5S, 6S)-6-[(R)-1-hydroxyethyl]-2-[(2S, 4S)-2-[N-(2-hydroxyethylpyrrolidin-3-yl]pyrrolidin-4-ylthio]-1-methyl-1-carbapen-2-em-3-carboxylate diastereomer A. By using the compound thus obtained without purification, the same procedure as in Example 1-2) was carried out to obtain the above-identified compound (564 mg, yield: 11.1%).

IR (KBr)cm$^{-1}$: 3400, 1750, 1590, 1380
NMR (D$_2$O)δ: 1.21(3H,d,J=7Hz), 1.28(3H,d,J=6Hz), 1.63(1H,m), 1.94(1H,m), 2.40(1H,m), 2.70(1H,m), 2.83(1H,m), 3.17(1H,m), 3.36(4H,m), 3.40–3.60(5H,m), 3.72(1H,dd,J=6,8Hz), 3.87(2H,m), 3.98(1H,m), 4.23(2H,m) UV λ$_{max}$ (0.1M 3-morpholinopropanesulfonic acid buffer solution, pH7.0): 299 nm (ε: 8450)

EXAMPLE 8

(1R, 5S, 6S)-6-[(R)-1-hydroxyethyl]-2-[(2S, 4S)-2-[N-(2-hydroxyethyl)pyrrolidin-3-yl]pyrrolidin-4-ylthio]-1-methyl-1-carbapen-2-em-3-carboxylic acid diastereomer B

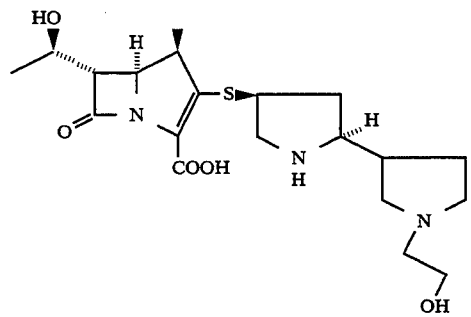

The same procedure as in Example 1-1) was carried out by using (2S, 4S)-2-[N-(2-hydroxyethyl)pyrrolidin-3-yl]-4-mercaptopyrrolidine diastereomer B (190 mg, 0.5 mmol, compound of Reference Example 8) to obtain p-nitrobenzyl (1R, 5S, 6S)-6-[(R)-1-hydroxyethyl]-2-[(2S, 4S)-2-[N-(2-hydroxyethylpyrrolidin-3-yl]pyrrolidin-4-ylthio]-1-methyl-1-carbapen-2-em-3-carboxylate diastereomer B. By using the compound thus obtained without purification, the same procedure as in Example 1-2) was carried out to obtain the above-identified compound (76 mg, yield: 35.7%).

IR (KBr)cm$^{-1}$: 3400, 1750, 1590, 1380
NMR (D$_2$O)δ: 1.21(3H,d,J=7Hz), 1.28(3H,d,J=6Hz), 1.6(1H,m), 1.94(1H,m), 2.40(1H,m), 2.7(1H,m), 2.83(1H,m), 3.17(1H,m), 3.36( 4H,m), 3.4–3.5(5H,m), 3.7(1H,dd,J=6,8Hz), 3.87(2H,m), 3.98(1H,m), 4.23(2H,m) UV λ$_{max}$ (0.1M 3-morpholinopropanesulfonic acid buffer solution, pH7.0): 299 nm (ε: 6710)

REFERENCE EXAMPLE 1

(2R, 4S)-4-acetylthio-N-(p-nitrobenzyloxycarboxycarbonyl)-2-[(2S, 4R)-N-(p-nitrobenzyloxycarbonyl)-2-(p-nitrobenzyloxycarbonyl)pyrrolidin-4-ylmethyl]pyrrolidine

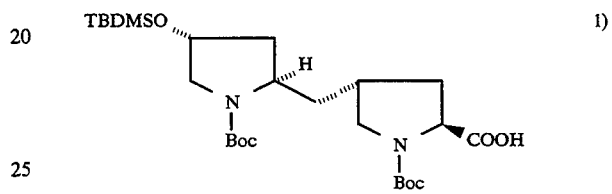

1)

Pyridinium dichromate was added to a solution of (2R, 4R)-N-tert-butoxycarbonyl-2-[(2S, 4R)-N-tert-butoxycarbonyl-2-(hydroxymethyl)pyrrolidin-4-ylmethyl]-4 -(tert-butyldimethylsiloxy)pyrrolidine (3.00 g, 5.84 mmol, compound of Reference Example 2–6) in N,N-dimethylformamide (30 ml) and stirred at room temperature for 14 hours. Ethyl acetate was added to the reaction solution and washed sequentially with water and a saturated sodium chloride aqueous solution, then dried over anhydrous sodium sulfate and concentrated. The residue was purified by silica gel flash column chromatography (Wakogel ™ C-300, 80 ml, n-hexane-ethyl acetate (1:1)) to obtain (2R, 4R)-N-tert-butoxycarbonyl-2-[(2S, 4R)-N-tert-butoxycarbonyl-2-carboxypyrrolidin-4-ylmethyl]-4-(tert-butyldimethylsiloxy)pyrrolidine (1.77 g, yield: 57%).

NMR (CDCl$_3$)δ: 0.09(6H,s), 0.86(9H,s), 1.45(18H,s), 1.64–1.71(2H,m), 1.87–2.16(2H,m), 2.23(1H,m), 2.57(1H,m), 2.97(1H,m), 3.27–3.56(3H,m), 3.89(2H,m), 4.30–4.41(2H,m)

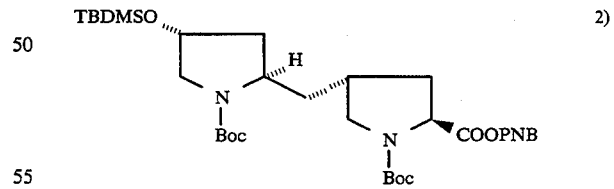

2)

To a solution of the compound obtained by the above reaction (2.00 g, 3.79 mmol), p-nitrobenzyl alcohol (640 mg, 4.18 mmol) and 4-(N,N-dimethylamino)pyridine (460 mg, 379 mmol) in methylene chloride, a solution of dicyclohexylcarbodiimide (0.86 g, 4.18 mmol) in methylene chloride (4 ml) was dropwise added under cooling with ice. The temperature of the reaction solution was returned to room temperature, and the solution was stirred at the same temperature for 5 hours.

After precipitates were filtered off, the filtrate was concentrated. The residue was purified by silica gel flash column chromatography (Wakogel ™ C-300, 100 ml, n-hexane-ethyl acetate (1:1)) to obtain (2R, 4R)-N-tertbutoxycarbonyl-2-[(2S, 4R)-N-tert-butoxycarbonyl-2-(p-nitrobenzyloxycarbonyl)pyrrolidin-4-ylmethyl]-4-(tertbutyldimethylsiloxy)pyrrolidine (1.40 g, yield: 56%).

NMR (CDCl₃)δ: 0.09(6H,s), 0.86(9H,s), 1.45(18H,s), 1.85–2.35( 6H,m), 2.88–3.10(1H,m), 3.30–3.55(2H,m), 3.65–3.90(3H,m) , 4.25–4.52(2H,m), 5.18–5.34(2H,m), 7.50(2H,m), 8.23(2H,m)

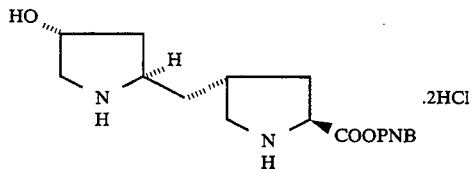

3)

To the compound obtained by the above reaction (1.40 g, 2.11 mmol), an about 3N hydrogen chloride-methanol solution was added and stirred at room temperature for 4 hours. The reaction mixture was concentrated under reduced pressure to obtain (2R, 4R)-4-hydroxy-2-[(2S, R)-2-(p-nitrobenzyloxycarbonyl )pyrrolidin-4-ylmethyl]pyrrolidine dihydrochloride (812 mg, yield: 91%).

NMR (D₂O)δ: 1.77–2.15(3H,m), 2.17–2.34(2H,m), 2.37–2.50(2H,m), 3.05–3.17(1H,m), 3.25–3.40(2H,m), 3.46–3.52(1H,dd,J=4.29,12.86Hz) , 3.71–3.75(1H,m), 4.61–4.75(2H,m) , 5.39(1H,d,J=13.2Hz), 5.45(1H,d,J=13.19Hz), 7.65(2H,d,J=8.58Hz), 8.28 ( 2H,d,J=8.91Hz )

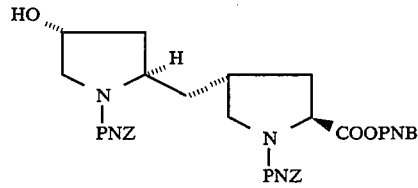

4)

To a solution of the compound obtained by the above reaction (812 mg, 1.92 mmol) and 4,6-dimethyl-2-(4-nitrobenzyloxycarbonylthio)pyrimidine (1.23 g, 3.84 mmol) in dioxane-water (8 ml:4 ml),-triethylamine (1.34 ml, 9.6 mmol) was added and stirred at room temperature for 2 hours. Ethyl acetate was added to the reaction solution. The organic layer was washed sequentially with a saturated sodium hydrogen carbonate aqueous solution and a saturated sodium chloride aqueous solution and then dried over anhydrous sodium sulfate and concentrated. The residue was purified by silica gel flash column chromatography (Wakogel TM C-300, 80 ml, ethyl acetate) to obtain (2R, 4R)-4-hydroxy-N-(p-nitrobenzyloxycarbonyl)-2-[(2S, 4R)-N-(p-nitrobenzyloxycarbonyl)-2-(p-nitrobenzyloxycarbonyl)pyrrolidin-4-ylmethyl]pyrrolidine (1.08 g, yield: 79%).

NMR (CDCl₃)δ: 1.65(1H,m), 2.05–2.40(6H,m), 3.07(1H,m), 3.48(1H,m), 3.60–3.78(2H,m) , 4.03(1H,m), 4.43(2H,m), 5.20(6H,m), 7.30–7.51(6H,m) , 8.12–8.30(6H,m)

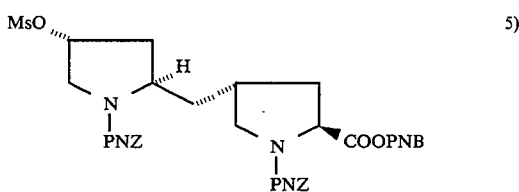

5)

Methanesulfonyl chloride (0.14 ml, 1.82 mmol) and triethylamine (0.28 ml, 1,98 mmol) were added to the solution of the compound obtained by the above reaction (1.08 g, 1.52 mmol) in methylene chloride (20 ml) under cooling with ice, and stirred at the same temperature for 1 hour, the reaction solution was washed sequentially with a saturated sodium hydrogen carbonate aqueous solution and a saturated sodium chloride aqueous solution, then dried and concentrated. The residue was purified by silica gel flash column chromatography (Wakogel TM C-300, 80 ml, ethyl acetate) to obtain (2R, 4R)-4-methanesulfonyloxy-N-(p-nitrobensyloxycarbonyl)-2-[(2S, 4R)-N-(p-nitrobensyloxycarbonyl)-2-(p-(nitrobenzyloxycarbonyl)pyrrolidin-4-ylmethyl]pyrrolidine (1.11 g, yield: 92%), NMR (CDCl₃)δ: 1.65–1.71(2H,m), 1.86–1.95(2H,m), 2.05–2.21(2H,m), 2.41–2.48(1H,m), 3.02(3H,s), 3.16(1H,m), 3.50–3.92(3H,m), 3.97–4.15(2H,m), 4.53(1H,m), 5.13–5.30(6H,m), 7.30–7.54(6H,m), 8.07–8.23(6H,m)

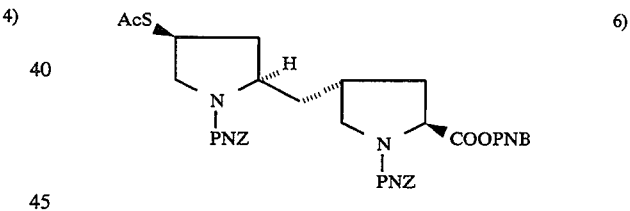

6)

Potassium thioacetate (480 mg, 4.23 mmol) was added to a solution of the compound obtained by the above reaction (1.11 g, 1.41 mmol) in N,N-dimethylformamide (20 ml) and stirred at 70° C. for 1 hour. Ethyl acetate was added to the reaction solution. The solution was washed with a saturated sodium chloride aqueous solution, then dried and concentrated. The residue was purified by silica gel flash column chromatography (Wakogel TM C-300, 80 ml, n-hexane-ethyl acetate (1:3)) to obtain (2R, 4S)-4-acetylthio-N-(p-nitrobenzyloxycarbonyl)-2-[(2S, 4R)-N-(p-nitrobenzyloxycarbonyl)-2-(p-nitrobenzyloxycarbonyl)pyrrolidin-4-ylmethyl]pyrrolidine (790 mg, yield: 73%).

NMR (CDCl₃)δ: 1.52–1.64(2H,m), 1.93–2.25(3H,m), 2.27–2.35(1H,m), 2.39(3H,s), 2.43–2.57(1H,m), 2.93–3.21(3H,m), 3.78–3.94(2H,m), 4.05–4.17(1H,m), 4.52–4.57(1H,m), 5.17–5.32(6H,m), 7.23–7.54(6H,m), 8.03–8.25(6H,m)

REFERENCE EXAMPLE 2

(2R, 4S)-4-acetylthio-2-[(2S, 4R)-2-hydroxymethyl-N-(p-nitrobenzyloxycarbonyl)pyrrolidin-4-ylmethyl]-N-(p-nitrobenzyloxycarbonyl)pyrrolidine

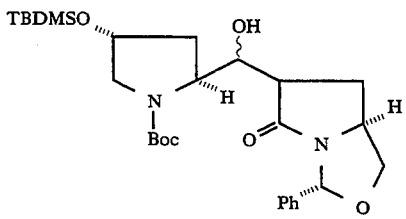
1)

To a solution of (2R, 5S)-8-oxo-2-phenyl-3-oxa-1-azabicyclo[3.3.0]octane (50 g, 246 mmol, J. Org. Chem., 51, 3140 (1986)) in tetrahydrofuran (1500 ml), lithium diisopropylamide (2M tetrahydrofuran-heptane solution, 147.6 ml, 295.2 mmol) was dropwise added at −78° C., and the reaction solution was stirred at the same temperature for 30 minutes. A solution of (2S, 4R)-N-tert-butoxycarbonyl-4-tert-butyldimethylsiloxyprolinal (61.0 g, 245.9 mmol) in tetrahydrofuran (400 ml) was dropwise added thereto, and the reaction solution was stirred at the same temperature for 30 minutes. Acetic acid (17.6 ml, 307.5 mmol) was dropwise added to the reaction solution. Then, the dry ice bath was removed and the reaction mixture solution was stirred for 30 minutes. To the reaction solution, ethyl acetate and 5% sodium hydrogen carbonate aqueous solution were added and the solution mixture was subjected to liquid separation and the aqueous layer was extracted with ethyl acetate. The organic layers were put together and washed with a saturated sodium chloride aqueous solution, then dried over anhydrous sodium sulfate and concentrated under reduced pressure. Ethyl acetate and n-hexane were added to the residue and the precipitated crystal was collected by filtration to obtain (2R, 5S)-7-[[(2S, 4R)-N-tert-butoxycarbonyl-4-(tert-butyldimethylsiloxy)pyrrolidin-2-yl](hydroxy)methyl]-8-oxo-2-phenyl-3-oxa-1azabicyclo[3.3.0]octane diastereomer A (14.0 g, yield: 11.3%). The filtrate was concentrated to obtain an oily diastereomer mixture (114.7 g, yield: 87.5%).

NMR (CDCl₃)δ: 0.03(6H,s), 0.80(9H,s), 1.38(9H,s), 2.00–2.54(4H,m), 3.18–3.58(3H,m), 3.90–4.36(5H,m), 4.37–4.50(1H,m), 6.20–6.30(1H,s), 7.25–7.40(5H,m)

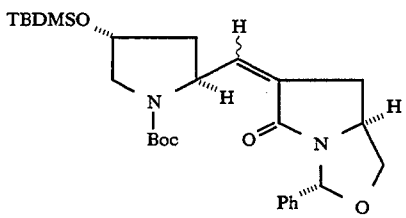
2)

The oily diastereomer mixture obtained by the above reaction (114.7 g, 215.34 mmol) was dissolved in a solution mixture of acetic anhydride (205 ml) and pyridine (205 ml), and the solution was stirred at room temperature for 16 hours. After the reaction solution was concentrated, ethyl acetate was added thereto. The solution was washed with a 5% sodium hydrogen carbonate aqueous solution, a saturated sodium chloride aqueous solution, then dried over anhydrous sodium sulfate and concentrated. Toluene (1,300 ml) and 1,8-diazabicyclo[5.4.0]undec-7-ene (57 ml, 384.14 mmol) were added to the residue and stirred at 70° C. under heating for 1 hour. The solvent was distilled off under reduced pressure and ethyl acetate was added to the residue. The solution was washed with a 5% sodium hydrogen carbonate aqueous solution and a saturated sodium chloride aqueous solution, dried over anhydrous sodium sulfate and concentrated. The residue was subjected to silica gel flash column chromatography (Wakogel ™ C-300, 400 ml, ethyl acetate-hexane (1:3)) to obtain (2R, 5S)-7-[(2S, 4R)-N-tert-butoxycarbonyl-4-(tertbutyldimethylsiloxy)pyrrolidin-2-ylmethylidene]-8-oxo-2-phenyl-3-oxa-1-azabicyclo[3.3.0]octane (71.48 g, yield: 56.5%).

NMR (CDCl₃)δ: 0.03(6H,s), 0.80(9H,s), 1.37(9H,s), 1.60–2.60(4H,m), 3.20–3.50(3H,m),-3.90–4.60(4H,m), 6.30(2H,m), 7.20–7.50(5H,m)

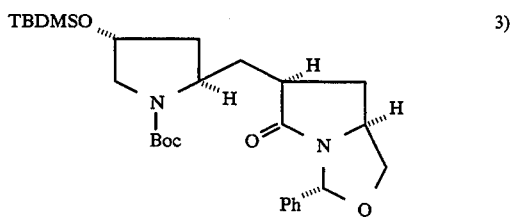
3)

To a solution of the compound obtained by the above reaction (71.48 g, 139 mmol) in ethanol (1,300 ml), 10% palladium-carbon catalyst (10.7 g) was added, and the reaction solution was stirred in a hydrogen gas stream for 36 hours. After the catalyst was filtered off, the solvent was distilled off under reduced pressure to obtain oily (2R, 5S, 7S)-7-[(2R, 4R)-tert-butoxycarbonyl-4-(tert-butyldimethylsiloxy)pyrrolidin-2-ylmethyl ]-8-oxo-2-phenyl-3-oxa-1-azabicyclo[3.3.0]octane (74.41 g, yield: 100%).

NMR (CDCl₃)δ: 0.03(6H,s), 0.80(9H,s), 1.40(9H,s), 1.50–2.30(5H,m), 2.90(1H,s), 3.30–3.50(3H,m), 4.00–4.40(5H,m), 6.30(1H,s), 7.20–7.50(5H,m)

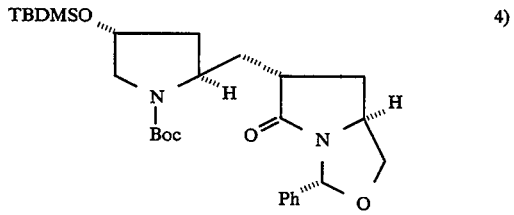
4)

To a solution of the compound obtained by the above reaction (74.41 g, 139 mmol) in tetrahydrofuran (1,300 ml), lithium diisopropylamide (2.0M tetrahydrofuran-heptane solution, 89.3 ml, 178.6 mmol) was dropwise added at −78° C., and the solution was stirred at the same temperature for 30 minutes. Methanol (7.5 ml) was dropwise added thereto and then the dry ice bath was removed. The solution was continued to stir until the temperature of the reaction solution became 0° C. Ethyl acetate and a saturated ammonium chloride aqueous solution were added to the reaction solution and the solution mixture was subjected to liquid separation. The aqueous layer was extracted with ethyl acetate. The organic layers were put together and washed with a saturated sodium chloride aqueous solution, then dried and concentrated. The residue was subjected to silica gel flash column chromatography (Wakogel TM C-300, 2,200 ml, ethyl acetate-heptane (1:3)) to obtain oily (2R, 5S, 7R)-7-[(2R, 4R)-N-tert-butoxycarbonyl-4-(tert-butyldimethylsiloxy)pyrrolidin-2-ylmethyl]-8-oxo-2-phenyl-3-oxa-1-azabicyclo[3.3.0]octane (56.95 g, yield: 79.4%).

NMR (CDCl₃)δ: 0.03(6H,s), 0.80(9H,s), 1.40(9H,s), 1.60-2.30(5H,m), 2.50(1H,m), 3.30(3H,m), 3.80-4.30(5H,m), 6.30(1H,s), 7.20-7.40(5H,m)

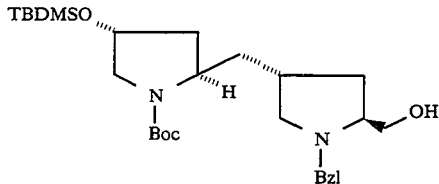

5)

A borane-dimethylsulfide complex (33.07 ml, 348.68 mmol) was dropwise added to a solution of the compound obtained by the above reaction (56.95 g, 110.22 mmol) in tetrahydrofuran (560 ml). The reaction solution was stirred at 70° C. under heating for 1 hour and then methanol (37 ml) was added thereto at 0° C. After stirring for a while, the solvent was distilled off under reduced pressure. The residue was dissolved in methanol (560 ml) and the solution was stirred at 80° C. under heating for 4 hours. The solvent was distilled off under reduced pressure to obtain N-benzyl-2-(hydroxymethyl)pyrrolidin-4-ylmethyl]-N-tert-butoxycarbonyl-4-(tert-butyldimethylsiloxy)pyrrolidine (56.42 g), which was used for the subsequent reaction without purification.

NMR (CDCl₃)δ: 0.03(6H,s), 0.80(9H,s), 1.40(9H,s), 1.50-2.10(7H,m), 2.80(1H,m), 3.00(1H,m), 3.20-3.40(5H,m), 3.60(1H,dd,J=2,5.5Hz), 3.90(1H,d,J=6Hz), 4.20(1H,m), 7.30(5H,s)

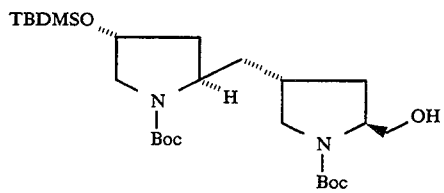

6)

Cyclohexene (5.0 ml) and a 20% palladium hydroxide-carbon catalyst (1.0 g, water content: about 30%) were added to a solution of the compound obtained by the above reaction (5.0 g) in ethanol (12 ml), and stirred and refluxed under heating in a nitrogen stream for 1 hour. After cooling, the catalyst was filtered off from the reaction mixture and the filtrate was concentrated under reduced pressure. The residue was dissolved in dioxane (50.0 ml) and water (25.0 ml) and a 2N sodium hydroxide aqueous solution (4.96 ml, 9.92 mmol) and di-tert-butyl dicarbonate (2.16 g, 9.90 mmol) were added thereto at room temperature and stirred for 1 hour. Dioxane was distilled off under reduced pressure from the reaction solution and 6N hydrochloric acid (1.7 ml, 10.2 mmol) was added and neutralized. The solution was extracted with ethyl acetate, then the organic layer was dried over magnesium sulfate and concentrated. The residue was subjected to silica gel column chromatography (Wakogel TM C-300, 200 ml, ethyl acetate-n-heptane (1:3)) to obtain (2R, 4R)-N-tert-butoxycarbonyl-2-[(2S, 4R)-N-tert-butoxycarbonyl-2-(hydroxymethyl)pyrrolidin-4-ylmethyl]-4-(tert-butyldimethylsiloxy)pyrrolidine (3.86 g, yield: 76%).

NMR (CDCl₃)δ: 0.08(6H,s), 0.88(9H,s), 1.46(18H,br s), 1.40-1.80(5H,m), 1.96(1H,m), 2.18(1H,m), 2.96(1H,m), 3.30-3.70(4H,m), 3.80-4.20(2H,m), 4.36(1H,m)

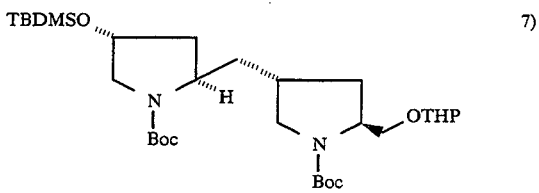

7)

3,4-dihydro-2H-pyran (0.24 ml, 2.68 mmol) and pyridinium tosylate (449 mg, 1.79 mmol) were added to a solution of the compound obtained by the above reaction (0.92 g, 1.79 mmol) in methylene chloride (18.0 ml), and stirred at room temperature for 18 hours. The reaction solution was poured into a saturated sodium hydrogen carbonate aqueous solution and extracted with methylene chloride. The organic layer was dried over magnesium sulfate and concentrated under reduced pressure. The residue was subjected to silica gel column chromatography (Wakogel TM C-300, 100 ml, ethyl acetate-n-heptane (1:3)) to obtain (2R, 4R)-N-tert-butoxycarbonyl-4-(tert-butyldimethylsiloxy)-2-[(2S, 4R)-N-tert-butoxycarbonyl-2-[(tetrahydropyran-2-yl)oxymethyl]pyrrolidin-4ylmethyl]pyrrolidine (1.03 g, yield: 96%).

NMR (CDCl₃)δ: 0.05(6H,s), 0.86(9H,s), 1.46(18H,s), 1.4-2.4(13H, m), 2.90(1H,m), 3.20-4.10(9H,m), 4.32(1H,m), 4.60(1H,m)

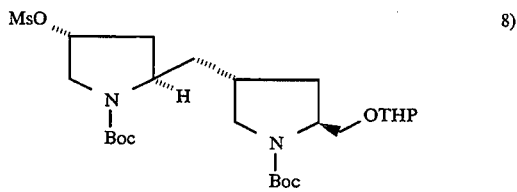

8)

1M tetrabutylammonium fluoride (tetrahydrofuran solution) (40,0 ml, 40,0 mmol) was added to a solution of the compound obtained by the above reaction (20.0 g, 33.4 mmol) in tetrahydrofuran (200 ml) at room temperature and stirred for 1 hour, The reaction solution was concentrated under reduced pressure and then diluted with ethyl acetate. The solution was washed with a sodium chloride aqueous solution, then dried over magnesium sulfate and concentrated under reduced pressure. Methanesulfonyl chloride (5.17 ml, 66.8 mmol) and triethylamine (11.2 ml, 80.2 mmol) were added to a solution of the residue in methylene chloride (200 ml) under cooling with ice and stirred for 30 minutes. The reaction solution was poured into a saturated sodium hydrogen carbonate aqueous solution and extracted with methylene chloride. The solution was dried over magnesium sulfate and concentrated under reduced pressure. The residue was subjected to silica gel column chromatography (Wakogel TM C-300, 600 ml, ethyl acetate-n-heptane (1:1)) to obtain (2R, 4R)-N-tert-butoxycarbonyl-2-[(2S, 4R)-N-tert-butoxycarbonyl-2-[(tetrahydropyran-2-yl)oxymethyl]pyrrolidin-4-ylmethyl]-4-methanesulfonyloxypyrrolidine (16.3 g, yield: 87%).

NMR (CDCl₃)δ: 1.45(9H,s), 1.48(9H,s), 1.4–2.6(13H,m), 2.90(1H,m), 3.03(3H,s), 3.40–4.10(9H,m), 4.57(1H,m), 5.18(1H,m)

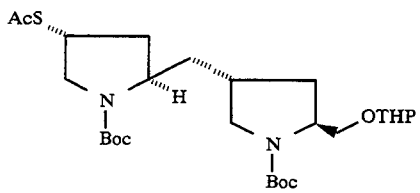
9)

A mixture of the compound obtained by the above reaction (16.3 g, 29.0 mmol), potassium thioacetate (9.9 g, 86.8 mmol) and N,N-dimethylformamide (326 ml) was stirred at 80° C. for 2.5 hours. After cooling, the reaction solution was poured into a sodium chloride aqueous solution and extracted with ethyl acetate. The solution was dried over magnesium sulfate and concentrated. The residue was subjected to silica gel column chromatography (Wakogel TM C-300, 600 ml, ethyl acetate-n-heptane (1:3)) to obtain (2R, 4S)-4-acetylthio-N-tert-butoxycarbonyl-2-[(2S, 4R)-N-tert-butoxycarbonyl-2-[(tetrahydropyran-2-yl)oxymethyl]pyrrolidin-4-ylmethyl]pyrrolidine (14.2 g, yield: 90%).

NMR (CDCl₃)δ: 1.45(18H,s), 1.40–1.80(10H,m), 2.08(2H,m), 2.32(3H,s), 2.52(1H,m), 3.07(1H,m), 3.50(4H,m), 3.60–4.10(6H,m), 4.58(1H,m)

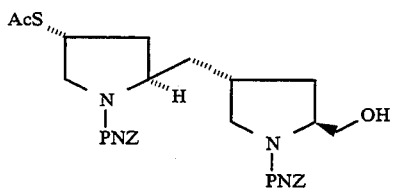
10)

The compound obtained by the above reaction (460 mg, 0.85 mmol) was dissolved in a 3.5M hydrogen chloride-methanol solution (2.5 ml, 9.1 mmol) and stirred at room temperature for 3 hours. The solution was concentrated under reduced pressure and the residue thus obtained was dissolved in water (4.5 ml). A solution of triethylamine (0.59 ml, 4.24 mmol) and 4,6-dimethyl-2-(p-nitrobenzyloxycarbonylthio)pyrimidine (641 mg, 2.0 mmol) in dioxane (4.5 ml) was added thereto at room temperature and stirred for 2 hours. The reaction solution was poured into a saturated sodium hydrogen carbonate aqueous solution and extracted with ethyl acetate. The organic layer was dried over magnesium sulfate and concentrated under reduced pressure. The residue was subjected to silica gel column chromatography (Wakogel TM C-300,100 ml, ethyl acetate-n-heptane (3:1)) to obtain the above-identified compound (387 mg, yield: 74%).

NMR (CDCl₃)δ: 1.50–2.00(4H,m), 2.00–2.40(2H,m), 2.34(3H,s), 2.59(1H,m), 2.90–4.20(9H,m), 5.22(4H,m), 7.50(4H,m), 8.20(4H,m)

REFERENCE EXAMPLE 3

(2R, 4S)-4-acetylthio-2-[( 2R, 4S)-2-methyl-N-(p-nitrobenzyloxycarbonyl)pyrrolidin-4-ylmethyl]-N-(p-nitrobenzyloxycarbonyl)pyrrolidine

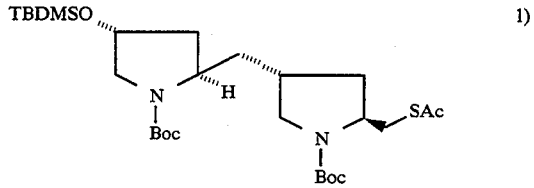
1)

To a solution of (2R, 4R)-N-tert-butoxycarbonyl-2[(2S, 4R)-N-tert-butoxycarbonyl-2-hydroxymethyl-pyrrolidin-4-ylmethyl]-4-(tert-butyldimethylsiloxy)pyrrolidine (1.29 g, 2.51 mmol, compound of Reference Example 2-6) in methylene chloride (26.0 ml), methanesulfonyl chloride (0.23 ml, 3.01 mmol) and triethylamine (0.45 ml, 3.26 mmol) were added under cooling with ice and stirred for 30 minutes. A methanesulfonyl compound was obtained in the same manner as in Reference Example 2-8). Further, the compound thus obtained was treated with potassium thioacetate (0.86 g, 7.53 mmol) in N,N-dimethylformamide (26.0 ml) in the same manner as in Reference Example 2-9) and purified to obtain (2R, 4R)-2-[(2S, 4R)-2-acetylthiomethyl-N-tertbutoxycarbonylpyrrolidin-4-ylmethyl]-N-tert-butoxycarbonyl-4-(tert-butyldimethylsiloxy)pyrrolidine (1.37 g, yield: 95%).

NMR (CDCl₃)δ: 0.06(3H,s), 0.86(9H,S), 1.45(18H,s), 1.50–2.30(7H,m), 2.35(3H,s), 2.80–3.60(6H,m), 3.85(2H,m), 4.31(1H,m)

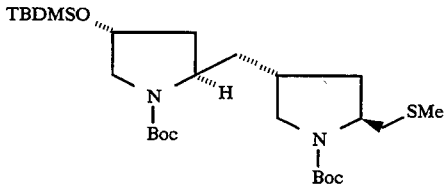
2)

A 2N sodium methoxide solution (1.44 ml, 2.88 mmol) was added to a solution of the compound obtained by the above reaction (1.37 g, 2.39 mmol) in methanol (26.0 ml) at room temperature and stirred for 1 hour. Then, methyl iodide (0.74 ml, 11.9 mmol) was added thereto and further stirred for 30 minutes. The reaction solution was concentrated under reduced pressure, and the residue was subjected to silica gel column chromatography (Wakogel TM C-300) to obtain (2R, 4R)-N-tert-butoxycarbonyl-2-[(2S, 4R)-N-tert-butoxycarbonyl-2-(methylthiomethyl)pyrrolidin-4-ylmethyl]-4-(tert-butyldimethylsiloxy)pyrrolidine (0.86 g, yield: 66%).

NMR (CDCl₃)δ: 0.05(3H,s), 0.06(3H,s), 0.87(9H,s), 1.46(18H,s) , 1.60–2.20(6H,m), 2.16(3H,s), 2.40(1H,m), 2.92(2H,m) , 3.16(2H,m), 3.52(2H,m), 3.90(2H,m), 4.32(1H,m)

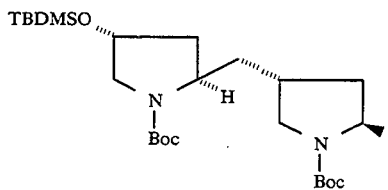

Raney nickel alloy (manufactured by Kawaken Fine Chemical, NDT-65, about 7 g) was added to a solution of the compound obtained by the above reaction (0.86 g, 1.58 mmol) in ethanol (7.0 ml), and refluxed under heating in a nitrogen stream overnight. The catalyst was filtered off from the reaction mixture with celite and concentrated under reduced pressure to obtain (2R, 4R)-N-tert-butoxycarbonyl-2-[(2R, 4S)-N-tert-butoxycarbonyl-2-methylpyrrolidin-4-ylmethyl]-4-(tertbutyldimethylsiloxy)pyrrolidine (478 mg, yield: 61%).

NMR (CDCl$_3$)δ: 0.03(6H,s), 0.84(9H,s), 1.13(3H,m), 1.40(2H,m), 1.43(18H,s), 1.66(3H,m), 1.97(1H,m), 2.19(1H,m), 2.87(1H,m), 3.20–3.60(3H,m), 3.84(2H,m), 4.30(1H,m)

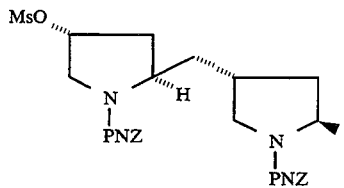

The compound obtained by the above reaction (478 mg, 0.96 mmol) was dissolved in a 3.2M hydrogen chloride-dioxane solution and stirred for 2 hours at room temperature. The reaction solution was concentrated under reduced pressure. An aqueous solution of the residue thus obtained (4.8 ml) was treated with a solution of triethylamine (0.67 ml, 4.80 mmol) and 4,6-dimethyl-2-(p-nitrobenzyloxycarbonylthio)pyrimidine (612 mg, 1.92 mmol) in dioxane (4.8 ml) in the same manner as in Reference Example 2-10). A solution of the compound thus obtained (about 557 mg, 1.03 mmol) in methylene chloride (9.4 ml) was treated with methanesulfonyl chloride (89 μl, 1.23 mmol) and triethylamine (0.20 ml, 1.54 mmol) in the same manner as in Reference Example 2-8) and purified to obtain (2R, 4R)-4-methanesulfonyloxy-2-[(2R, 4S)-2-methyl-N-(p-nitrobenzyloxycarbonyl)pyrrolidin-4-ylmethyl]-N-(p-nitrobenzyloxycarbonyl)pyrrolidine (472 mg, yield: 79%).

NMR (CDCl$_3$)δ: 1.46(3H,d,J=6Hz), 1.75(2H,m), 1.94(2H,m), 2.04–2.40(2H,m), 2.53(1H,m), 3.04(3H,s), 3.62(2H,m), 4.07(4H,m), 5.23(5H,m), 7.50(4H,d,J=8Hz), 8.21(4H,d,J=8Hz)

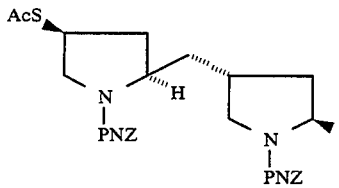

The compound obtained by the above reaction (470 mg, 0.76 mmol) was treated with potassium thioacetate (260 mg, 2.28 mmol) in N,N-dimethylformamide (9.4 ml) in the same manner as in Reference Example 2-9)

and purified to obtain the above-identified compound ( 423 mg, yield: 93%).

NMR (CDCl$_3$)δ: 1.18(3H,m), 1.40–1.80(4H,m), 2.00–2.40(2H,m), 2.34(3H,s), 2.57(1H,m), 3.00(1H,m), 3.22(1H,m), 3.62(1H,m), 3.88(2H,m), 4.08(2H,m), 5.20(4H,br s), 7.50(4H,d,J=8Hz), 8.21(4H,d,$J$=8Hz)

REFERENCE EXAMPLE 4

(2S, 4S)-2-[N-(2-hydroxyethyl)piperidin-4-yl]-4-mercaptopyrrolidine dihydrochloride

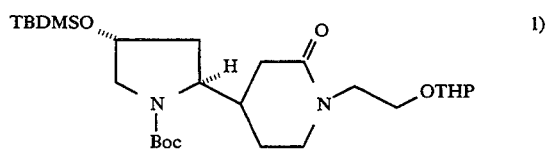

60% sodium hydride (1.30 g, 32.5 mmol) was added to a solution of (2S, 4R)-N-tert-butoxycarbonyl-4-tert-butyldimethylsiloxy-2-(2-piperidon-4-yl)pyrrolidine (10.0 g, 25.1 mmol, compound of Reference Example 39-3 of U.S. patent application Ser. No. 07/780,142) in tetrahydrofuran (500 ml) at room temperature, and stirred for 1 hour. Further, 2-(2-tetrahydropyranyloxy)ethyl iodide (12.3 g, 50 mmol) was added thereto and refluxed for 18 hours under stirring and heating. After cooling, the solvent was distilled off under reduced pressure. Water was added to the residue and extracted with ethyl acetate (150 ml). The organic layer was washed with a saturated sodium chloride aqueous solution and dried over anhydrous sodium sulfate. The solvent was distilled off under reduced pressure and the residue was subjected to silica gel column chromatography (Wakogel TM C-300, 200 ml, heptane-ethyl acetate (1:1→0:100)) to obtain (2S, 4R)-N-tert-butoxycarbonyl-4-tert-butyldimethylsiloxy-2-[N-[2-(2-tetrahydropyranyloxy)ethyl]-2-piperidon-4-yl]pyrrolidine (8.60 g, yield: 65.9%).

NMR (CDCl$_3$)δ: 0.05(6H,s), 0.86(9H,s), 1.3–2.5(13H,m), 1.45(9H,s), 3.1–4.1(11H,m), 4.3(1H,m), 4.57(1H,m)

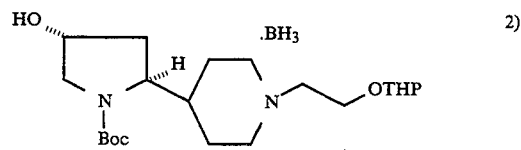

A borane-dimethyl sulfide complex (15.94 ml, 0.168 mol) was slowly dropwise added to a solution of the compound obtained by the above reaction (41.3 g, 80 mmol) in tetrahydrofuran (400 ml) under stirring and cooling with ice. After completion of the dropwise addition, the solution was refluxed for 2 hours under stirring and heating. After cooling, methanol (50 ml) was dropwise added to the solution under cooling with ice and stirring and the solvent was distilled off under reduced pressure. To a solution of the residue thus obtained in tetrahydrofuran (300 ml), a solution of 1M tetrabutylammonium fluoride in tetrahydrofuran (88 ml, 88 mmol) was dropwise added under cooling with ice and stirred for 3 hours. A saturated ammonium chloride aqueous solution (100 ml) was added to the reaction solution and then, ethyl acetate (300 ml) and water (200 ml) were added thereto. The organic layer was washed with a saturated sodium chloride aqueous solution and dried over anhydrous sodium sulfate. The solvent was distilled off under reduced pressure and the residue thus obtained was subjected to silica gel column chromatography (Wakogel ™ C-300, 600 ml, heptane-ethyl acetate (1:1→0:100)) to obtain a (2S, 4R)-N-tert-butoxycarbonyl-4-hydroxy-2-[N-[2-(2-tetrahydropyranyloxy)ethyl]piperidin-4-yl]pyrrolidineborane complex (20.17 g, yield: 62.9%).

NMR (CDCl$_3$)δ: 1.2–1.5(15H,m)1.46(9H,s), 2.45–3.35(5H,m), 3.4–4.25(6H,m), 4.38(1H,m), 4.58(1H,m)

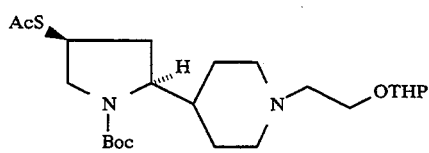

3)

Triethylamine (7.7 ml, 55 mmol) was added to a solution of the compound obtained by the above reaction (20.1 g, 50 mmol) in methylene chloride (500 ml) under stirring and cooling with ice, and then methanesulfonyl chloride (4.29 ml, 55 mmol) was dropwise added thereto. The solution was stirred at the same temperature for 1 hour. The reaction solution was washed with water, dried over anhydrous sodium sulfate and the solvent was distilled off under reduced pressure. Potassium thioacetate (17.1 g, 150 mmol) was added to a solution of the residue thus obtained in N,N-dimethylformamide (350 ml) and stirred at a temperature of 50° C.–60° C. for 15 hours in a nitrogen stream. The reaction solution was poured into water and extracted with ethyl acetate (200 ml). The organic layer was washed sequentially with water and a saturated sodium chloride aqueous solution and dried over anhydrous sodium sulfate. The solvent was distilled off under reduced pressure and the residue thus obtained was subjected to silica gel column chromatography (Wakogel ™ C-300, 300 ml, heptane-ethyl acetate (2:1→0:100), methylene chloride-methanol (1:9→1:20)) to obtain (2S, 4S)-4-acetylthio-N-tert-butoxycarbonyl-2-[N-[2-(2-tetrahydropyranyloxy)ethyl]piperidin-4-yl]pyrrolidine (13.76 g, yield: 61.7%).

NMR (CDCl$_3$)δ: 1.2–1.9(12H,m), 1.45(9H,s), 1.9–2.15(3H,m), 2.32(3H,s), 2.56–2.65(2H,m), 2.82–3.1(3H,m), 3.45–3.6(2H,m), 3.68–3.93(4H,m), 4.12(1H,m), 4.59(1H,m)

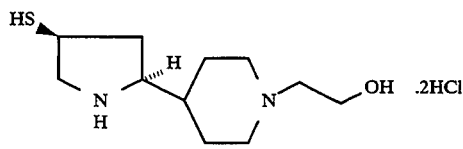

4)

A solution of the compound obtained by the above reaction ( 580 mg, 1.26 mmol) in 1.5N hydrogen chloride-methanol (5 ml) was refluxed under heating and stirring for 1.5 hours. After cooling, the solvent was distilled off under reduced pressure and ethanol (10 ml) was added to the residue. Then, the solvent was again distilled off under reduced pressure. Ethanol (10 ml) was added to the residue and the solution was left for 18 hours. Crystals precipitated was collected by filtration and washed with ethanol followed by drying to obtain the above-identified compound (250 mg, yield: 65.6%).

NMR (D$_2$O)δ: 1.5–1.9(3H,m), 1.9–2.2(3H,m), 2.72(1H,m), 2.95–3.15(2H,m), 3.15–3.32(2H,m), 3.32–3.55(2H,m), 3.55–3.82(4H,m), 3.82–3.98(2H,m)

REFERENCE EXAMPLE 5

(2S, 4S)-2-[3-hydroxymethyl-N-(p-nitrobenzyloxycarbonyl)pyrrolidin-4-yl]-4-mercapto-N-(p-nitrobenzyloxycarbonyl)pyrrolidine diastereomer A

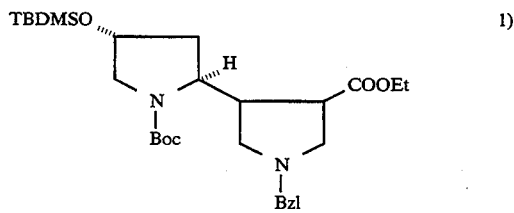

1)

N-benzyl-N-(methoxymethyl)trimethylsilylmethylamine (40.2 g, 135.6 mmol, purity: 80%) was added to a solution of ethyl (E)-3-[(2S, 4R)-N-tert-butoxycarbonyl-4-tert-butyldimethylsiloxypyrrolidin-2-yl]acrylate (37.4 g, 93.5 mmol, compound of Reference Example 1-4 of U.S. patent application Ser. No. 07/674,971) in methylene chloride (190 ml) in a nitrogen stream, and a 1M trifluoroacetic acid-methylene chloride solution (9.35 ml, 9.35 mmol) was dropwise added under cooling with ice. The reaction solution was stirred at room temperature for 1.5 hours, and poured into a saturated sodium hydrogen carbonate aqueous solution. The organic layer was washed sequentially with water, a 10% citric acid aqueous solution, water and a saturated sodium chloride aqueous solution, dried over anhydrous magnesium sulfate and concentrated under reduced pressure to obtain a (2S, 4R)-N-tert-butoxycarbonyl-4-tert-butyldimethylsiloxy-2-(N-benzyl-3-ethoxycarbonylpyrrolidin-4-yl)pyrrolidine diastereomer mixture (50.2 g, yield: 100%).

IR (KBr)cm$^{-1}$: 2950, 2925, 2850, 1730, 1695, 1390

NMR (CDCl$_3$)δ: 0.05(6H,s), 0.85(9H,s), 1.24(3H,t,J=7Hz), 1.43(9H,s), 1.93(2H,m), 2.4–3.0(8H,m), 3.2(1H,m), 3.6(2H,br s), 4.05(2H,q,J=7Hz), 4.35(1H,m), 7.2–7.3(5H,m)

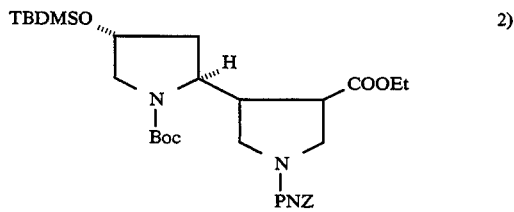

2)

To a solution of the compound obtained by the above reaction (50.17 g, 94.2 mmol) in dry methanol (630 ml), 10% palladium-carbon catalyst (50 g) and then ammonium formate (29.7 g, 471 mmol) were added thereto and refluxed under heating for 1 hour. After completion of the reaction, the catalyst was filtered off and the solution was concentrated under reduced pressure to obtain a yellow oily substance (38.05 g). The oily substance was dissolved in a mixture of dioxane (500 ml) and a saturated sodium hydrogen carbonate aqueous solution (500 ml) and 4,6-dimethyl-2-(p-nitrobenzyloxycarbonylthio)pyrimidine (30.2 g, 94.6 mmol) was added thereto and stirred at room temperature for 17 hours. Ethyl acetate (1,000 ml) was added to the reaction solution, and the organic layer was washed sequentially with water, 10% citric acid aqueous solution and a saturated sodium chloride aqueous solution, dried over anhydrous magnesium sulfate, and concentrated under reduced pressure. The residue thus obtained was subjected to silica gel column chromatography (Wakogel TM C-300, ethyl acetate-heptane (1:3)) to obtain a (2S, 4R)-N-tert-butoxycarbonyl-4-butyldimethylsiloxy-2-[3-ethoxycarbonyl-N-(p-nitrobenzyloxycarbonyl)pyrrolidin-4-yl]pyrrolidine diastereomer mixture (33 g, yield: 61.8%).

IR (KBr)cm$^{-1}$: 1730, 1710, 1690, 1520

NMR (CDCl$_3$)δ: 0.05(6H,s), 0.85(9H,s), 1.25(3H,t,J=7Hz), 1.43(9H,s), 1.73(1H,m), 1.99(1H,m), 2.92-3.18(3H,m), 3.52-3.69(2H,m), 3.79(1H,m), 4.14(3H,m), 4.34(1H,m), 5.20(2H,s), 7.51(2H,d,J=9Hz), 8.21(2H,d,$^J$=9Hz)

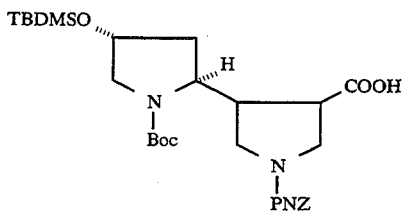

The compound obtained by the above reaction (33 g, 53 mmol) was dissolved in methanol (300 ml) and a 1N sodium hydroxide aqueous solution (106 ml, 106 mmol) was dropwise added thereto under cooling with ice and stirred at room temperature for 1 hour, after completion of the reaction, a 1N hydrochloric acid aqueous solution (106 ml, 106 mmol) was added thereto and the solvent was distilled off under reduced pressure. The residue was extracted with ethyl acetate-(300 ml) and washed with a saturated sodium chloride aqueous solution, dried over anhydrous magnesium sulfate and concentrated under reduced pressure. The residue thus obtained was subjected to silica gel column chromatography (Wakogel TM C-300, 1-2% methanol-chloroform) to obtain (2S, 4R)-N-tert-butoxycarbonyl-4-tert-butyldimethylsiloxy-2-[3-carboxy-N-(p-nitrobenzyloxycarbonyl)pyrrolidin-4-yl]pyrrolidine diastereomer A (7.42 g, yield: 23.6%) and diastereomer B (17.89 g, yield: 56.8%).

Diastereomer A

IR (KBr)cm$^{-1}$: 1730, 1710, 1695:, 1510

NMR (CDCl$_3$)δ: 0.05(6H,s), 0.85(9H,s), 1.48(9H,s), 1.71(1H,m), 2.10(1H,m), 2.51(1H,m), 3.02-3.16(3H,m), 3.67-3.87 (4H,m), 4.28-4.44(2H,m), 5.21(2H,s), 7.51(2H,d,J=9Hz), 8.21(2H,d,J=9Hz)

Diastereomer B

IR (KBr)cm$^{-1}$: 1730, 1710, 1695 , 1510

NMR ( CDCl$_3$)δ: 0.05(6H,s), 0.85(9H,s), 1.44(9H,s), 1.72( 1H,m) , 2.0(1H,m), 3.01(2H,m), 3.19(2H,m), 3.46( 1H,m) , 3.61(2H,m), 3.84(1H,m), 4.16(1H,m), 4.34( 1H,m) , 5.22(2H,s) , 7.51(2H,d,J=9Hz), 8.22( 2H,d,J=9Hz)

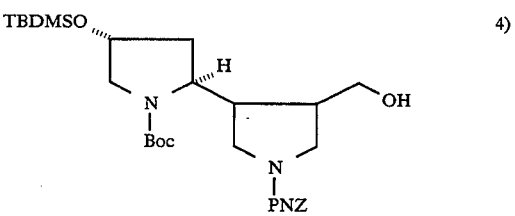

Diastereomer A obtained by the above reaction (5.85 g, 9.85 mmol) was dissolved in tetrahydrofuran (80 ml) and a diborane-dimethyl sulfide complex (1.8 ml, 19 mmol) was dropwise added thereto under cooling with ice. The solution was stirred at room temperature for 2.5 hours. Methanol (5 ml) was added thereto and concentrated under reduced pressure. The residue thus obtained was dissolved in ethyl acetate and washed sequentially with water and a saturated sodium chloride aqueous solution, then dried over anhydrous magnesium sulfate and concentrated under reduced pressure to obtain (2S, 4R)-N-tert-butoxycarbonyl-4-tert-butyldimethylsiloxy-2-[3-hydroxymethyl-N-(p-nitrobenzyloxycarbonyl)pyrrolidin-4 -yl]pyrrolidine diastereomer A (5.85 g, yield: 100%), which was used for the subsequent reaction without purification.

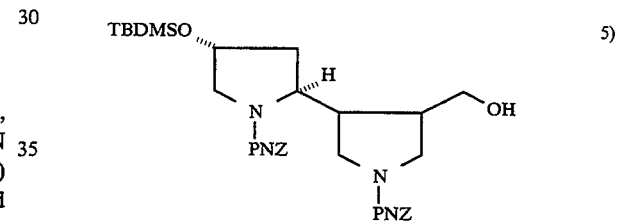

The compound obtained by the above reaction (5.85 g, 10.1 mmol) was dissolved in methylene chloride (20 mi) and trifluoroacetic acid (10.11 ml, 131 mmol) was dropwise added thereto under cooling with ice. The solution was stirred at the same temperature for 2 hours. The reaction solution was poured into a mixture of dioxane (130 ml) and a 1N sodium hydroxide aqueous solution (130 ml) and adjusted to pH9.5. Then, 4,6-dimethyl-2-(p-nitrobenzyloxycarbonylthio)pyrimidine (3.87 g, 12.1 mmol) was added thereto and stirred for 17 hours. The reaction solution was poured into ethyl acetate (260 ml), washed sequentially with water, a saturated sodium hydrogen carbonate aqueous solution and a saturated sodium chloride aqueous solution. The solution was dried over anhydrous magnesium sulfate and concentrated under reduced pressure. The residue thus obtained was subjected to silica gel column chromatography (Wakogel TM C-300, 2% methanol-chloroform) to obtain (2S, 4R)-4-tert-butyldimethylsiloxy-2-[3 -hydroxymethyl-N-(p-nitrobenzyloxycarbonyl)pyrrolidin-4-yl ]-N-(p-nitrobenzyloxycarbonyl)-pyrrolidine diastereomer A (4.79 g, yield: 72.1%).

IR (KBr)cm$^{-1}$: 3450, 2950, 2900, 2800, 1700, 1520

NMR (CDCl$_3$)δ: 0.05(6H,s), 0.83(9H,s), 1.76(2H,m), 2.03(1H,m), 2.3-2.7(2H,m), 3.1-3.4(3H,m) , 3.55-3.75(4H,m), 4.3-4.6(2H,m), 5.21(4H,s), 7.51(4H,d,J=9Hz), 8.21(4H,d,J=9Hz)

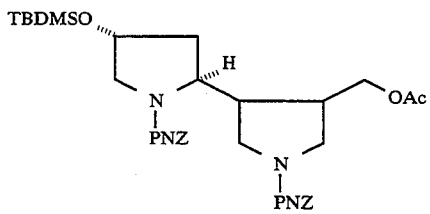

6)

The compound obtained by the above reaction (5.22 g, 7.92 mmol) was dissolved in a mixture of pyridine (10.44 ml) and acetic anhydride (20.88 ml) and stirred at room temperature for 2 hours. The solution was concentrated under reduced pressure, and the residue was dissolved in ethyl acetate (100 ml), followed by washing sequentially with water, 10% citric acid aqueous solution and a saturated sodium chloride aqueous solution. The solution was dried over anhydrous magnesium sulfate and concentrated under reduced pressure to obtain a light-yellow foamy substance of (2S, 4R)-2-[3-acetoxymethyl-N-(p-nitrobenzyloxycarbonyl)pyrrolidin-4-yl]-4-tert-butyldimethylsiloxy-N-(p-nitrobenzyloxycarbonyl)pyrrolidine diastereomer A (5.69 g, yield: 100%), which was used for the subsequent reaction without purification.

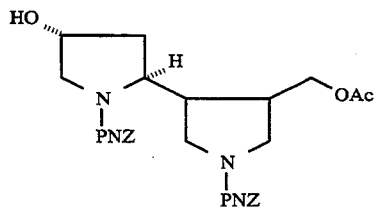

7)

The compound obtained by the above reaction (5.69 g, 8.12 mmol) was dissolved in tetrahydrofuran (69 ml) and a solution of tetrabutylammonium fluoride (3.12 g, 8.9 mmol) in tetrahydrofuran (9 ml) was dropwise added thereto under cooling with ice, and stirred at the same temperature for 2 hours. Ethyl acetate (140 ml) was added to the reaction solution and washed sequentially with a saturated ammonium chloride aqueous solution, water and a saturated sodium chloride aqueous solution. The solution was dried over anhydrous magnesium sulfate and concentrated under reduced pressure to obtain (2S, 4R)-2-[3-acetoxymethyl-N-(p-nitrobenzyloxycarbonyl)pyrrolidin-4-yl]-4-hydroxy-N-(p-nitrobenzyloxycarbonyl)pyrrolidine diastereomer A (5.27 g, yield: 100%), which was used for the subsequent reaction without purification.

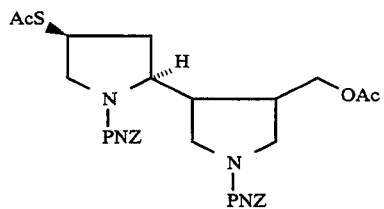

8)

The compound obtained by the above reaction (5.27 g, 8.98 mmol) was dissolved in tetrahydrofuran (100 ml) and triethylamine (2.48 ml, 17.9 mmol) and then methanesulfonyl chloride (1.4 ml, 17.9 mmol) were dropwise added thereto under cooling with ice and stirred at the same temperature for 1 hour. Ethyl acetate (200 ml) was added to the reaction solution and washed sequentially with a saturated sodium hydrogen carbonate aqueous solution, water, a saturated citric acid aqueous solution and a saturated sodium hydrogen carbonate aqueous solution, then dried over anhydrous magnesium sulfate. The solution was concentrated under reduced pressure, and the foamy and oily substance thus obtained was dissolved in N,N-dimethylformamide (100 ml). Sodium iodide (1,129 mg, 7.53 mmol) and potassium thioacetate (1,290 mg, 11.3 mmol) were added thereto and stirred in a nitrogen stream at 70° C. for 5 hours. Ethyl acetate (350 ml) was added to the reaction solution and washed sequentially with water and a saturated sodium chloride aqueous solution. The solution was dried over anhydrous magnesium sulfate and concentrated under reduced pressure. The residue thus obtained was subjected to silica gel column chromatography (Wakogel TM C-300, ethyl acetate-heptane (1:1)) to obtain (2S, 4S)-2-[3-acetoxymethyl-N-(p-nitrobenzytoxycarbonyl)pyrrolidin-4-yl]-4-acetylthio-N-(p-nitrobenzyloxycarbonyl)pyrrolidine diastereomer A (3.94 g, yield: 90.4%).

IR (KBr)cm$^{-1}$: 1740, 1700, 1520

NMR (CDCl$_3$)δ: 1.64(2H,m), 2.05(3H,S), 2.35(3H,S), 2.4–2.65(3H,m), 3.1(1H,m), 3.29(2H,m), 3.6–3.8(3H,m), 3.9–4.3(4H,m), 5.21(4H,s), 7.51 ( 4H,d,J=9Hz ), 8.22(4H,d,J=9Hz)

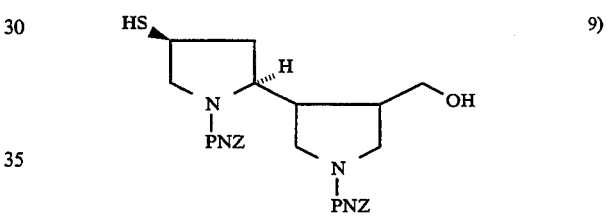

9)

The compound obtained by the above reaction (3.94 g, 6.11 mmol) was dissolved in methanol (16 ml) and a 2.5N hydrochloric acid-methanol solution was dropwise added under cooling with ice. The solution was stirred at room temperature for 17 hours. The solvent was distilled off under reduced pressure, and the residue was dissolved in ethyl acetate. The solution was washed sequentially with water and a saturated sodium chloride aqueous solution, dried over anhydrous magnesium sulfate, and concentrated under reduced pressure to obtain the above-identified compound (3.34 g, yield: 97.5%).

REFERENCE EXAMPLE 6

(2S, 4S)-2-[3-hydroxymethyl-N-(p-nitrobenzyloxycarbonyl)pyrrolidin-4-yl]-4-mercapto-N-(p-nitrobenzyloxycarbonyl)pyrrolidine diastereomer B

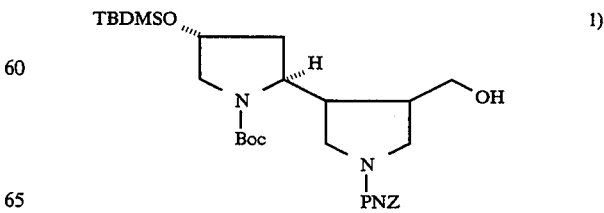

1)

The same procedure as in Reference Example 5-4) was carried out by using (2S, 4R)-N-tert-butoxycarbonyl-4-tert-butyldimethylsiloxy-2-[3-carboxy-N-(p-diastereomer B (16.26 g, 27.4 mmol, compound of Reference Example 5-3)) to obtain (2S, 4R)-N-tert-butoxycarbonyl-4-diastereomer B (14.14 g, yield=89.1%), which was used for the subsequent reaction without purification.

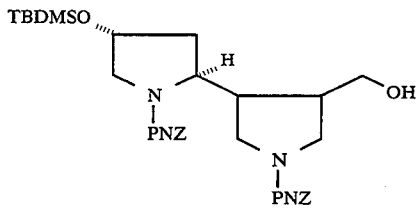

2)

The same procedure as in Reference Example 5-5) was carried out by using the compound obtained by the above reaction (14.14 g, 24.4 mmol) to obtain (2S, 4R)-4-tert-butyldimethylsiloxy-2-[3-hydroxymethyl-N-(p-nitrobenzyloxycarbonyl)pyrrolidin-4-yl]-N-(p-nitrobenzyloxycarbonyl)pyrrolidine diastereomer B (13.78 g, yield: 85.8%).

IR (KBr)cm⁻¹: 3450, 2950, 2900, 1700, 1520
NMR (CDCl₃)δ: 0.06(6H,s), 0.84(9H,s), 1.8(1H,m), 1.97(1H,m), 2.17(1H,m), 2.85(1H,m), 3.18(1H,m), 3.33(2H,m), 3.5–3.8(5H,m), 4.27(1H,m), 4.35(1H,m), 5.21(4H,m), 7.51(4H,d,J=9Hz), 8.21(4H,d,J=9Hz)

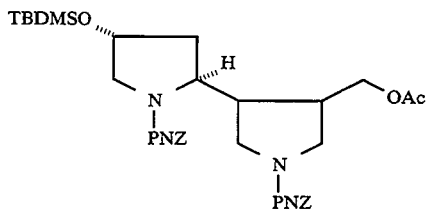

3)

The same procedure as in Reference Example 5-6) was carried out by using the compound obtained by the above reaction (13.78 g, 20.9 mmol) to obtain a light-yellow foamy substance of (2S, 4R)-3-[3-acetoxymethyl-N-(p-nitrobenzyloxycarbonyl)pyrrolidin-4-yl]-4-tert-butyldimethylsiloxy-N-(p-nitrobenzyloxycarbonyl)pyrrolidine diastereomer B (13.84 g, yield: 94.4%), which was used for the subsequent reaction without purification.

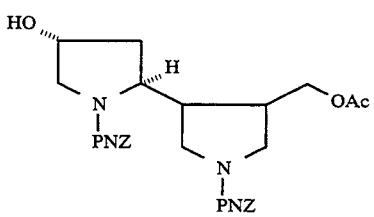

4)

The same procedure as in Reference Example 5-7) was carried out by using the compound obtained by the above reaction (13.84 g, 19.7 mmol) to obtain (2S, 4R)-2-[3-acetoxymethyl-N-(p-nitrobenzyloxycarbonyl)pyrrolidin-4-yl]-4-hydroxy-N-(p-nitrobenzyloxycarbonyl)-pyrrolidine diastereomer B (12.04 g, yield: 100%), which was used for the subsequent reaction without purification.

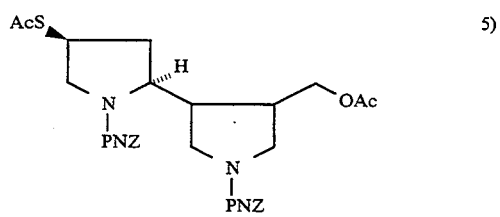

5)

The same procedure as in Reference Example 5-8) was carried out by using the compound obtained by the above reaction (12.04 g) to obtain (2S, 4S)-2-[3-acetoxymethyl-N-(p-nitrobenzyloxycarbonyl)pyrrolidin-4-yl]-4-acetylthio-N-(p-nitrobenzyloxycarbonyl)pyrrolidine diastereomer B (8.49 g, yield: 75.1%).

IR (KBr)cm⁻¹: 1740, 1700, 1520
NMR (CDCl₃)δ: 1.71(2H,m), 2.06(3H,s), 2.35(3H,s), 2.4–2.65(3H,m), 3.1(1H,m), 3.24(2H,m), 3.55(1H,m), 3.71(1H,m), 3.85(1H,m), 3.97(1H,m), 4.1–4.25(3H,m), 5.22(4H,s), 7.52(4H,d,J=9Hz), 8.22(4H,d,J=9Hz)

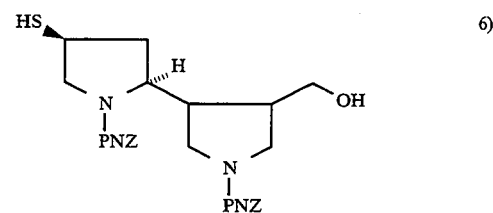

6)

The same procedure as in Reference Example 5-9) was carried out by using the compound obtained by the above reaction (8.49 g, 13.2 mmol) to obtain the above-identified compound (6.44 g, yield: 84.8% ).

REFERENCE EXAMPLE 7

(2S, 4S)-2-[N-(2-hydroxyethyl)pyrrolidin-3-yl]-4-mercaptopyrrolidine diastereomer A dihydrochloride

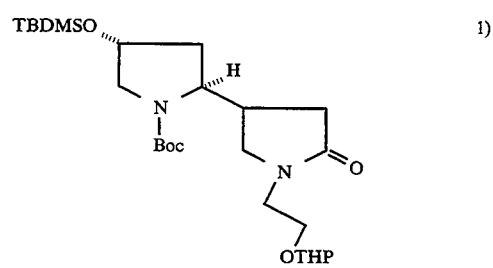

1)

The same procedure as in Reference Example 4-1) was carried out by using (2S, 4R)-N-tert-butoxycarbonyl-4-tert-butyldimethylsiloxy-2-(2-pyrrolidon-4-yl)pyrrolidine diastereomer A (37.04 g, 80 mmol, compound of Reference Example 12 of U.S. patent application Ser. No. 07/674,971) to obtain (2S, 4R)-N-tert-butoxycarbonyl-4-tert-butyldimethylsiloxy-2-[N-[2-(tetrahydropyran-2-yloxy)ethyl]-2-pyrrolidon-4-yl]pyrrolidine diastereomer A (43.45 g, yield: 100%).

IR (KBr)cm⁻¹: 3450, 2940, 1690, 1390, 1250, 1160, 1115, 1030, 835, 770
NMR (CDCl₃)δ: 0.06(6H,s), 0.86(9H,s), 1.48(9H,s), 1.50–1.90(9H,m), 2.21(1H,dd,J=6,18Hz), 2.46(1H,dd,J=8,18Hz), 2.95(1H,br m), 3.24(2H,m), 3.50(5H,m), 3.81(2H,m), 4.10(1H,br m), 4.29(1H,m), 4.2(1H,m)

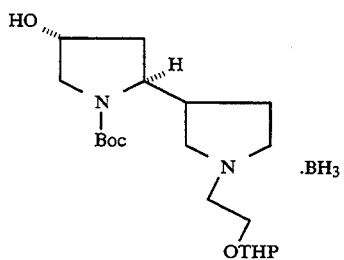

The same procedure as in Reference Example 4-2) was carried out by using the compound obtained by the above reaction (43.45 g) to obtain (2S, 4R)-N-tert-butoxycarbonyl-4-hydroxy-2-[N-[2-(tetrahydropyran-2-yloxy)ethyl]pyrrolidin-3-yl]pyrrolidine-borane complex diastereomer A (20.47 g, yield: 64%).

IR (KBr)cm$^{-1}$: 3430, 2940, 2350, 1680, 1390, 1160, 1120, 1030, 970, 870, 770 NMR (CDCl$_3$)δ: 1.48(9H,s), 1.50-2.10(10H,m), 2.13(1H,m), 2.38(1H,m), 2.70(1H,m), 2.94(1H,m), 3.05(2H,m), 3.30(3H,m), 3.57(2H,m), 3.90(2H,m), 4.15(2H,m), 4.44(1H,m), 4.62(1H,m)

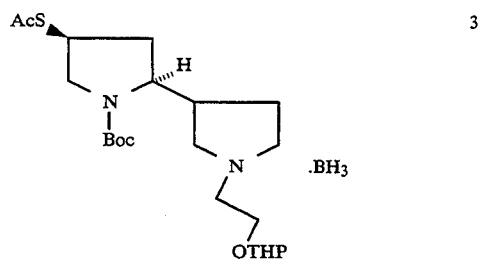

The same procedure as in Reference Example 4-3) was carried out by using the compound obtained in the above reaction (20.47 g, 51.4 mmol) to obtain (2S, 4S)-4-acetylthio-N-tert-butoxycarboxyl-2-[N-[2-(tetrahydropyran-2-yloxy)ethyl]pyrrolidin-3-yl]pyrrolidine-borane complex diastereomer A (15.8 g, yield: 68.6%).

IR (KBr)cm$^{-1}$: 3400, 2950, 2370, 1690, 1390, 1160, 1120, 1030, 870, 630

NMR (CDCl$_3$)δ: 1.47(9H,s), 1.50-1.85(8H,m), 1.98(1H,m), 2.20(1H,m), 2.34(3H,s), 2.45-2.68(2H,m), 3.06(4H,m), 3.30(2H,m), 3.52(1H,m), 3.87(3H,m), 4.12(3H,m), 4.61(1H,m)

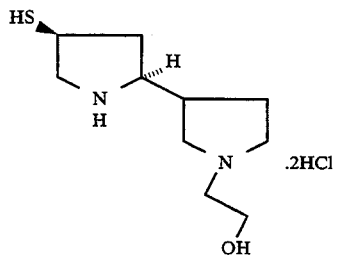

The same procedure as in Reference Example 4-4) was carried out by using the compound obtained by the above reaction (5.45 g, 11.9 mmol)-to obtain the above-identified compound (3.5 g, yield: 100%) as a crude crystal, which was used for the subsequent reaction without further purification.

REFERENCE EXAMPLE 8

(2S, 4S)-2-[N-(2-hydroxyethyl)pyrrolidin-3-yl]-4-mercaptopyrrolidine diastereomer B dihydrochloride

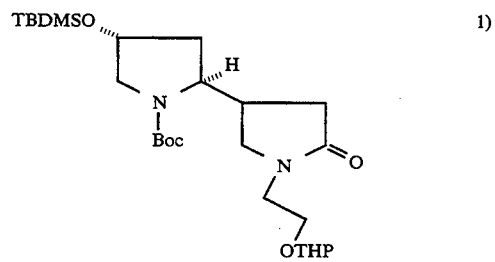

The same procedure as in Reference Example 4-1) was carried out by using (2S, 4R)-N-tert-butoxycarbonyl-4-tert-butyldimethylsiloxy-2-(2-pyrrolidon-4-yl)pyrrolidine diastereomer B (385 mg, 1 mmol, compound of Reference Example 12 of U.S. patent application Ser. No. 07/674,971) to obtain (2S, 4R)-N-tert-butoxycarbonyl-4-tert-butyldimethylsiloxy-2-[N-[2-(tetrahydropyran-2-yloxy)ethyl]-2-pyrrolidon-4-yl]pyrrolidine diastereomer B (500 mg), which was used for the subsequent reaction without purification.

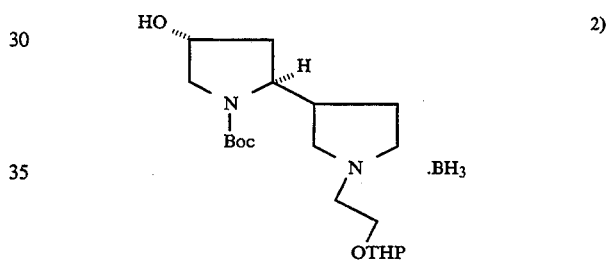

The same procedure as in Reference Example 4-2) was carried out by using the compound obtained by the above reaction (500 mg) to obtain (2S, 4R)-N-tert-butoxycarbonyl-4-hydroxy-2-[N-[2-(tetrahydropyra-2-yloxy)ethyl]pyrrolidin-3-yl]pyrrolidine-borane complex diastereomer B (420 mg), which was used for the subsequent reaction without purification.

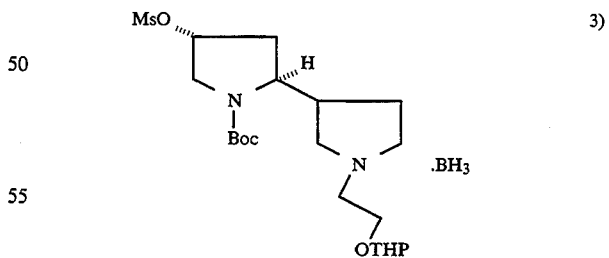

The compound obtained by the above reaction (420 mg) was dissolved in tetrahydrofuran (5 ml), and triethylamine (0.21 ml, 1.5 mmol) and then methanesulfonyl chloride (0.12 ml, 1.5 mmol) were dropwise added thereto under cooling with ice and stirred at the same temperature for 2 hours. Ethyl acetate (10 ml) was added to the reaction solution and washed sequentially with water and a saturated sodium chloride aqueous solution. The solution was dried over anhydrous magnesium sulfate and concentrated under reduced pressure. The residue thus obtained was subjected to silica gel column chromatography (Wakogel ™ C-300, 1% methanol-chloroform) to obtain (2S, 4R)-N-tert-butoxycarbonyl-4-methanesulfonyloxy-2-[N-[2-(tetrahydropyran-2-yloxy)ethyl]pyrrolidin-3-yl]pyrrolidine-borane complex diastereomer B (333.4 mg, yield: 70%).

NMR (CDCl3)δ: 1.48(9H,s), 1.5–2.10(10H,m), 2.13(1H,m), 2.38(1H,m), 2.7(1H,m), 2.8(3H,s), 2.94(1H,m), 3.05(2H,m), 3.3(3H,m), 3.57(2H,m), 3.9(2H,m), 4.15(2H,m), 4.44(1H,m), 4.62(1H,m)

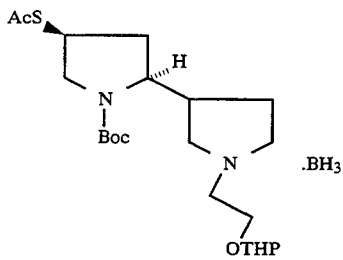

4)

The same procedure as in Reference Example 4-3) was carried out by using the compound obtained by the above reaction (333 mg, 0.7 mmol) to obtain (2S, 4S)-4-acetylthio-N-tert-butoxycarbonyl-2-[N-[2-(tetrahydropyran-2-yloxy)ethyl]pyrrolidin-3-yl]pyrrolidine-borane complex diastereomer B (226 mg, yield: 70.7%).

NMR (CDCl3)δ: 1.47(9H,s), 1.5–1.8(8H,m), 1.98(1H,m), 2.20(1H,m), 2.34(3H,s), 2.45(2H,m), 3.05(4H,m), 3.30(2H,m), 3.52(1H,m), 3.87(3H,m), 4.12(3H,m), 4.61(1H,m)

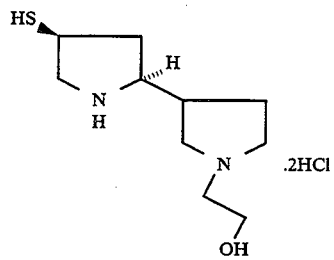

5)

The same procedure as in Reference Example 4-4) was carried out by using the compound obtained by the above reaction (226 mg, 0.5 mmol) to obtain the above-identified compound (190 mg), which was used for the subsequent reaction without purification.

What is claimed is:

1. A compound of the formula:

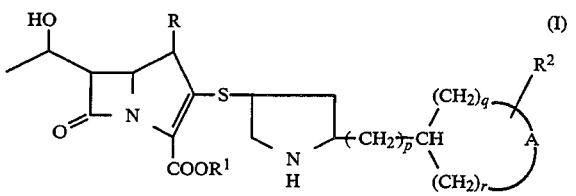

(I)

wherein R is a hydrogen atom or a methyl group, $R^1$ is a hydrogen atom or a negative charge, $R^2$ is a lower alkyl group, a lower alkyl group substituted with a hydroxyl group or —COOR$^3$ (wherein R$^3$ is a hydrogen atom or a lower alkyl group), A is =NH, =NR$^4$ or =N(R$^4$)R$^5$ (wherein each of R$^4$ R$^5$R$^4$ and R$^5$ which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and q+r≦6; or a pharmaceutically acceptable salt or ester thereof with the proviso that when A is =N+(R$^4$)R$^5$, R$^1$ is a negative charge.

2. The compound according to claim 1, wherein R is a methyl group.

3. The compound according to claim 1, wherein R$^2$ is a lower alkyl group substituted with a hydroxyl group.

4. The compound according to claim 1, wherein R$^2$ is a hydroxymethyl group.

5. The compound according to claim 1, wherein p is 0 or 1.

6. The compound according to claim 1, wherein p is 1.

7. The compound according to claim 1, wherein each of q and r, which may be the same or different, is 1 or 2.

8. The compound according to claim 1, wherein A is =NH.

9. The compound according to claim 1, wherein A is =NR$^4$ or =N(R$^4$)R$^5$ (wherein R$^4$ is a lower alkyl group substituted with a hydroxyl group and R$^5$ is a lower alkyl group or a lower alkyl group substituted with a hydroxyl group).

10. The compound according to claim 1, wherein a steric configuration in a carbapenem structure is (5R, 6S, 8R) or (1R, 5S, 6S, 8R).

11. The compound according to claim 1, which is:

(1R, 5S, 6S)-2-[(2R, 4S)-2-[(2S, 4R)-2-carboxypyrrolidin-4-ylmethyl]pyrrolidin-4-ylthio]-6-[(R)-1-hydroxyethyl]-1-methyl-1-carbapen-2-em-3-carboxylic acid, (1R, 5S, 6S)-6-[(R)-1-hydroxyethyl]-2-[(2R, 4S)-2-[(2S, 4R)-2-hydroxymethylpyrrolidin-4-ylmethyl]pyrrolidin-4-ylthio]-1-methyl-1-carbapen-2-em-3-carboxylic acid, (1R, 5S, 6S)-6-[(R)-1-hydroxyethyl]-1-methyl-2-[(2R, 4S)-2-[(2R, 4S)-2-methylpyrrolidin-4-ylmethyl]pyrrolidin-4-ylthio]-1-carbapen-2-em-3-carboxylic acid, (1R, 5S, 6S)-6-[(R)-1-hydroxyethyl]-2-[(2S, 4S)-2-[N-(2-hydroxyethyl)piperidin-4-yl]pyrrolidin-4-ylthio]-1-methyl-1-carbapen-2-em-3-carboxylic acid, (1R, 5S, 6S)-6-[(R)-1-hydroxyethyl]-2-[(2S, 4S)-2-(3-hydroxymethylpyrrolidin-4-yl)pyrrolidin-4-ylthio]-1-methyl-1-carbapen-2-em-3-carboxylic acid or (1R, 5S, 6S)- 6-[(R)-1-hydroxyethyl]-2-[(2S, 4S)-2-[N-(2-hydroxyethyl)pyrrolidin-3-yl]pyrrolidin-4-ylthio]-1-methyl-1-carbapen-2-em-3-carboxylic acid.

12. The compound according to claim 1, which is (1R, 5S, 6S)-6-[(R)-1-hydroxyethyl]-2-[(2R, 4S)-2-[(2S, 4R)-2-hydroxymethylpyrrolidin-4-ylmethyl]pyrrolidin-4-ylthio]-1-methyl-1-carbapen-2-em-3-carboxylic acid.

13. An antibacterial agent comprising an antibacterially effective amount of the compound of the formula:

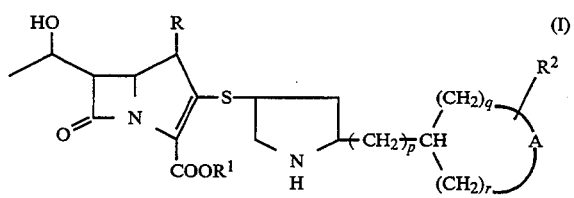

wherein R is a hydrogen atom or a methyl group, $R^1$ is a hydrogen atom or a negative charge, $R^2$ is a lower alkyl group, a lower alkyl group substituted with a hydroxyl group or $-COOR^3$ (wherein $R^3$ is a hydrogen atom or a lower alkyl group), A is $=NH$, $=NR^4$ or $=N(R^4)R^5$ (wherein each of $R^4$ $R^5 R^4$ and $R^5$, which may be the same or different, is a lower alkyl group or a lower alkyl group substituted with a hydroxyl group), p is an integer of from 0 to 3, and each of q and r which may be the same or different, is an integer of from 0 to 5, provided that q and r are not simultaneously 0 and $q+r \leqq 6$; or a pharmaceutically acceptable salt or ester thereof, and a pharmaceutically acceptable carrier or diluent.

* * * * *